US007355099B2

(12) United States Patent
Carozzi et al.

(10) Patent No.: US 7,355,099 B2
(45) Date of Patent: Apr. 8, 2008

(54) AXMI-004, A DELTA-ENDOTOXIN GENE AND METHODS FOR ITS USE

(75) Inventors: Nadine Carozzi, Raleigh, NC (US); Tracy Hargiss, Cary, NC (US); Michael G. Koziel, Raleigh, NC (US); Nicholas B. Duck, Apex, NC (US); Brian Carr, Raleigh, NC (US)

(73) Assignee: Athenix Corporation, Research Triangle Park, NC (US)

( * ) Notice: Subject to any disclaimer, the term of this patent is extended or adjusted under 35 U.S.C. 154(b) by 199 days.

(21) Appl. No.: 10/782,020

(22) Filed: Feb. 19, 2004

(65) Prior Publication Data

US 2004/0197916 A1 Oct. 7, 2004

Related U.S. Application Data

(60) Provisional application No. 60/448,810, filed on Feb. 20, 2003.

(51) Int. Cl.
*A01H 5/00* (2006.01)
*A01H 5/10* (2006.01)
*C12N 15/82* (2006.01)
*C12N 1/21* (2006.01)
*C12N 15/32* (2006.01)

(52) U.S. Cl. .................. 800/302; 435/418; 435/252.3; 435/320.1; 424/93.2; 536/23.71

(58) Field of Classification Search .................. None
See application file for complete search history.

(56) References Cited

U.S. PATENT DOCUMENTS

| 5,866,784 | A | 2/1999 | Van Mellaert et al. |
|---|---|---|---|
| 5,908,970 | A | 6/1999 | Van Mellaert et al. |
| 6,172,281 | B1 | 1/2001 | Van Mellaert et al. |
| 6,177,615 | B1 | 1/2001 | Baum |
| 6,833,449 | B1 * | 12/2004 | Barton et al. ............ 536/23.71 |

OTHER PUBLICATIONS

Lazar et al, 1988, Mol. Cell. Biol. 8:1247-1252.*
Hill et al, 1998, Biochem. Biophys. Res. Comm. 244:573-577.*
Guo et al, 2004, Proc. Natl. Acad. Sci. USA 101: 9205-9210.*
de Maagd et al, 1999, Appl. Environ. Microbiol. 65:4369-4374.*
Tounsi et al, 2003, J. Appl. Microbiol. 95:23-28.*
Angsuthanasombat et al, 2001, J. Biochem. Mol. Biol. 34:402-407.*
Aaronson et al, 2001, FEMS Microbiol. Lett. 195:1-8.*
De Maagd et al, 2001, Trends Genet. 17:193-199.*
Jenkins et al. (1999) FEBS Letters 462:373-376.*
Rajamohan et al. (1996) J Biol. Chem. 271 (41) :25220-25226.*
Lee et al. (2001) FEBS Letters 497:108-112.*
Schwartz et al. (1997) Appl. Environ. Microbiol. 63(10): 3978-3984.*
Masson et al. (2002) Appl. Environ. Microbiol. 68(1):194-200.*
Kalman, et al., "Cloning of a Novel *cryIC*-type Gene from a Strain of *Bacillus thuringiensis* subsp. *galleriae*," *Applied and Enviromental Microbiology*, 1993, pp. 1131-1137, vol. 59, No. 4.
Honèe, G., et al., "Nucleotide Sequence of Crystal Protein Gene Isolated from *B. thuringiensis* subspecies *entomocidus* 60.5 Coding for a Toxin Highly Active Against *Spodoptera* Species," *Nucleic Acids Research*, May 13, 1988, p. 6240, vol. 16, No. 13.
Sanchis, V., et al., "Nucleotide Sequence and Analysis of the N-terminal Coding Region of the Spodoptera-active δ-endotoxin Gene of *Bacillus thuringiensis aizawai* 7.29," *Mol. Microbiol.*, 1989, pp. 229-238, vol. 3, No. 2.
NCBI Database Report for Accession No. AAA22343, 1991.
NCBI Database Report for Accession No. AAF37224, Direct Submission on Dec. 14, 1999.
NCBI Database Report for Accession No. AAM00264, Direct Submission on Mar. 16, 2001.
NCBI Database Report for Accession No. AAN16462, Direct Submission on Aug. 22, 2002.
NCBI Database Report for Accession No. CAA65457, Direct Submission on Mar. 18, 1996.

* cited by examiner

*Primary Examiner*—Anne Kubelik
(74) *Attorney, Agent, or Firm*—Alston & Bird LLP

(57) ABSTRACT

Compositions and methods for conferring pesticidal activity to bacteria, plants, plant cells, tissues and seeds are provided. Compositions comprising a coding sequence for a delta-endotoxin polypeptide are provided. The coding sequences can be used in DNA constructs or expression cassettes for transformation and expression in plants and bacteria. Compositions also comprise transformed bacteria, plants, plant cells, tissues, and seeds. In particular, isolated delta-endotoxin nucleic acid molecules are provided. Additionally, amino acid sequences corresponding to the polynucleotides are encompassed. In particular, the present invention provides for isolated nucleic acid molecules comprising nucleotide sequences encoding the amino acid sequences shown in SEQ ID NOS:3 and 5, and the nucleotide sequences set forth in SEQ ID NOS:1, 2, and 4, as well as variants and fragments thereof.

14 Claims, 3 Drawing Sheets

FIG. 1A

```
              *         400         *         420         *         440         *         460         *
AXMI-004 : YYWGGHRVTSHYVGGEN--IRSPLYGREANQEVP-RDFYFYGPVFKTLSKPTIRPLQQPAPAPPFNLRSLEGVEFHTPTGS-----FMYRERGSV : 431
cry1Ac   : YYWSGHQIMASPVGFSGPEFTFPLYGTMGNAAPQQRIVAQLGQGVYRTLSSTLYRPFNIGINNQQLSVLDGTEFAYGTSSNLPS-AVYRKSGTV : 407
cry1Ca   : FYWSGHRVISSLIGGGM--ITSPIYGREANQEPP-RSFTFNGPVFRTLSNPTIRLLQQPWPAPPFNLRGWEGVEFSTPTNS-----FTYRGRGTV : 406
cry2Aa   : GVSSGLIGATNLMHNFNCSTVLPPLSTPFVRSWLDSGTDREGVATSTNWQTESFQTTLSLRCGAFSARGNSNYFPDYFIRNISGVPLVIRNEDLT : 439
cry3Aa   : NYWSGNYVSTRPSIGSMDIITSPFYGNKSSEPVQ-MLEFNGEKVYRAVANTNLAVWPSAVYSGVIKVEFSQYNDQTDEASTQTYDSKRNVGAVSW : 458
cry1Ia   : NMWGGHKLEFRTIGGTLN-ISTQGSTNTSINPVTLPFTSRDVYRTESLAGLNLFLTQPVNGVPRVDFHWKFVTHPIASDMFYYPG-YAGIGTQLQ : 450
cry7Aa   : FYWSAHKVSFKKSEQSN-LYTTGIYGKTSGYISSGAYSFHGNDIYRTLAAPSVVVYPYTQMYG----VEQVEFYGVKGHVHYR----GDNKYDLTY : 437

*         480         *         500         *         520         *         540         *         560         *
AXMI-004 : DSFNELPPFNPVGLPHKVYSHRLCHATFVRKSG---TPYLITGAIFSWTHRSAEETNTIESNIITQIPLVKAYQIGSGTTVRKGPGFTGGDILRR : 523
cry1Ac   : DSLDEIPPQNNNVPPRQGFSHRLSHVSMFRSGFSNSSVSIIRAPMFSWIHRSAEFNNIIASDSITQIPAVKGNFLFNG-SVISGPGFTGGDLVRL : 501
cry1Ca   : DSLTELPPEDNSVPPREGYSHRLCHATFVQRSG---TPFLTTGVVFSWTDRSATLTNTIDPERINQIPLVKGFRVWGGTSVITGPGFTGGDILRR : 498
cry2Aa   : RPLHYNQIRNIESPSGTPGGARAYLVSHVHRKN-------NIYAANENGTMIHLAPEDYTGFTISPIHATQVMNQTRTFISEKFGNQGDSLRF : 525
cry3Aa   : DSIDQLPPETTDEPLEKGYSHQLNYVMCFLMQG-----SRGTIPVLTWTHKSVDFFWMIDSKKITQLPLVKAYKLQSGASVVAGPRFTGGDIIQC : 548
cry1Ia   : DSENELPPEATGQPNYESYSHRLSHIGLISASH------VKALVYSWTHRSADRTWTIEPNSITQIPILVKAFNLSSGAAVVRGPGFTGGDILRR : 538
cry7Aa   : DSIDQLPPDG--EPIHEKYTHRLCHATAIFKSTP--DYDMATIPIFSWTHRSAEYYNRIYPNKITKIPAVKMYKLDDPSTVVKGPGFTGGDLVKR : 528

*         580         *         600         *         620         *         640         *         660         *
AXMI-004 : TGPGTFGDMRININAPLSQRYRVRIRYASTTDLQFVTSINGTTINIG------NFPKTINMLNTLGSEGYRTVSFSTPFSFSNAQSIFRLG---- : 608
cry1Ac   : NSSGNNIQNRGYIEVPIHFPSTSTRYRIRFRYASSRDARVILTGAASTGVGGQVSVNMPLQKTMEIGENLTSRTFRYTDFSNPFSFRANPDIIGISEQP : 591
cry1Ca   : NTFGDFVSLQVNINSPITQRYRLRFRYASSRDARVILTGAASTGVGGQVSVNMPLQKTMEIGENLTSRTFRYTDFSNPFSFRANPDIIGISEQP : 593
cry2Aa   : EQSNTTARYTLRGNG---NSYNIYLRVSSIGNSTIRVTINGRVYYTVSN-------VNTTTNNDGVNDNGARFSDINIGNIVASDNTNVTLDIN--- : 608
cry3Aa   : TENGSAATIYVTPDVSYSQKTRARIHYASTSQITFTLSLDGAPFNQY------YPDKTIMKGDTLITYNSFNLASFSTPFELSGNNLQIGVTG-- : 634
cry1Ia   : TNTGTFGDIRVNINPPFAQRYRVRIRYASTTDLQFHTSINGKAINQG--------NFSATMNRGEDLDYKTFRTVGFTPFTSFLDVQSTFTIG-- : 623
cry7Aa   : GSTGYIGDIKATVNSPLSQKYRVRVRFRYAINVSGQFNVYINDKITIQT----KFQNTVETIGEGKDLITYGSFGYIEYSTTIQFPDEHPKITLHLS- : 618

*         680         *         700         *         720         *
AXMI-004 : --IQAFSGVQEVYVDKIEFIPVE---------------------------------------- : 629
cry1Ac   : ----FSGTAGVIIDRFEFIPVTATLEAEYNLERAQKAVNALFTSTNQLGLKTNVTDYHIDQVSNLV : 653
cry1Ca   : LFGAGSISSGELYIDKIEILLADATFEAESDLERAQKAVNALFTSSMQIGLKTDVTDYHIDQVSNLV : 660
cry2Aa   : ---VTLNSGTPFDLMNIMFVPTNLPPLY----------------------------------- : 633
cry3Aa   : -------LSAGDKVYIDKIEFIPVN-------------------------------------- : 652
cry1Ia   : --AWNFSSGNEVYIDRIEFVPVEVTYEAEYDFEKAQEKVTALFTSNPRGLKIDVKDYHIDQVSNLV : 688
cry7Aa   : -----DLSNNSSFYVDSIEFIPVDWNYAEKEKLEKAQKAVNTLFTE-GRNALQKDVIDYKVDQVSILV : 680
```

FIG. 1B

SEQUENCE LISTING

```
<160> NUMBER OF SEQ ID NOS: 11

<210> SEQ ID NO 1
<211> LENGTH: 2190
<212> TYPE: DNA
<213> ORGANISM: Bacillus thuringiensis

<400> SEQUENCE: 1
tatgatgata actttgacaa cagccgcatc cataacgtac tttttcaata ttaattgtat      60
ccaagcttat tttgtacaaa ttacacttta ttgtatgcat aatagtttct tattgattga     120
gcatataaga aaatttttc atatataagt gaaaatattt ttgcttttct tttttttatt     180
taggataaac tttacttgta aacacaagta aatagtttat tagagataga gcctcatttt     240
aaaatattta cgaatcctat ctataaaaat ctaattttaa aattattcct tttaaatgta     300
atgagtgaat tgaaggggaa atttaagaaa agtactaatc gaacttgttg tttgctaaaa     360
ataataaata taggaggaag aggtatgaat tcaaaggaac atgattatct aaaagtttgt     420
aatgatttaa gtgacgccaa tattaatatg gaacggtttg ataagaatga tgcactggaa     480
attggtatgt ccattgtatc tgaacttatt ggtatgattc caggcggaac agctttgcaa     540
tttgtgttta atcaattgtg gtctcgttta ggtgattctg gatggaatgc gttcatggaa     600
catgtggagg aattaattga tactaaaata gaagggtatg caaaaaataa agccttatct     660
gaattagcag gtatacaaag aaaccttgaa acatatatac aattacgtaa tgaatgggaa     720
```

-continued

```
aatgatattg aaaactcaaa ggctcaaggt aaggtagcta attactatga aagtcttgag      780
caggcggttg aaaggagtat gcctcaattt gcagtggaga attttgaagt accactttta      840
actgtctatg tgcaagctgc taatcttcat ttattattat taagagatgt ttcagtttat      900
ggaaagtgtt ggggatggtc ggagcagaaa attaaaattt attatgataa acagattaag      960
tatacccatg aatacacaaa tcattgtgta aattggtata ataaaggact tgagagatta     1020
aaaaataaag gttcttctta tcaagattgg tacaattata atcgtttccg tagagaaatg     1080
actcttactg ttttagatat cgttgcttta ttcccgcact atgatgtaca aacttatcca     1140
ataacaaccg ttgctcagct aacaagggaa gtttatacgg atcctttact taatttttaat     1200
cctaaattac attctgtgtc tcaattacct agttttagtg acatggaaaa tgcaacaatt     1260
agaactccac atctgatgga attttttaaga atgctaacaa tttatacaga ttggtatagt     1320
gtgggaagaa actattattg gggaggacat cgcgtgacgt cttaccatgt aggaggagag     1380
aatataagat caccctctata tggtagagag gcaaatcaag aggttcctag agatttttat     1440
ttttatggac ccgttttta gacgttatca agccgactc taagaccatt acagcagcct     1500
gcaccagctc ctccttttaa tttacgtagc ttagagggag tagaattcca cactcctaca     1560
ggtagtttta tgtatcgtga agaggatcg gtagattctt ttaatgagtt gccgcctttt     1620
aatccagttg ggtacctca taaggtatac agtcaccgtt tatgtcatgc aacgtttgtt     1680
cgtaaatctg gaccccctta tttaacaaca ggtgccatct tttcttggac acatcgtagt     1740
gctgaagaaa ccaatacaat tgaatcaaat attattacgc aaatcccgtt agtaaaagca     1800
tatcaaattg ggtcaggcac tactgtaagg aaaggaccag gattcacagg aggggatata     1860
cttcgaagaa caggtcctgg aacatttgga gatatgagaa taaatattaa tgcaccatta     1920
tctcaaagat atcgtgtaag gattcgttat gcttctacga cagatttaca atttgtcacg     1980
agtattaatg ggaccaccat taatattggt aacttcccga aaactattaa taatctaaat     2040
actttaggtt ctgagggcta tagaacagta tcgtttagta ctccatttag tttctcaaat     2100
gcacaaagca tatttagatt aggtatacaa gcattttctg gagttcaaga agtttatgtg     2160
gataaaattg aatttattcc tgttgaatag                                      2190
```

<210> SEQ ID NO 2
<211> LENGTH: 1890
<212> TYPE: DNA
<213> ORGANISM: Bacillus thuringiensis
<220> FEATURE:
<221> NAME/KEY: CDS
<222> LOCATION: (1)...(1890)

<400> SEQUENCE: 2

```
atg agt gaa ttg aag ggg aaa ttt aag aaa agt act aat cga act tgt       48
Met Ser Glu Leu Lys Gly Lys Phe Lys Lys Ser Thr Asn Arg Thr Cys
1               5                   10                  15 tgt ttg cta aaa ata ata aat ata gga gga aga ggt atg aat tca aag       96
Cys Leu Leu Lys Ile Ile Asn Ile Gly Gly Arg Gly Met Asn Ser Lys
            20                  25                  30 gaa cat gat tat cta aaa gtt tgt aat gat tta agt gac gcc aat att      144
Glu His Asp Tyr Leu Lys Val Cys Asn Asp Leu Ser Asp Ala Asn Ile
        35                  40                  45 aat atg gaa cgg ttt gat aag aat gat gca ctg gaa att ggt atg tcc      192
Asn Met Glu Arg Phe Asp Lys Asn Asp Ala Leu Glu Ile Gly Met Ser
    50                  55                  60 att gta tct gaa ctt att ggt atg att cca ggc gga aca gct ttg caa      240
Ile Val Ser Glu Leu Ile Gly Met Ile Pro Gly Gly Thr Ala Leu Gln
```

```
                65                  70                  75                  80
ttt gtg ttt aat caa ttg tgg tct cgt tta ggt gat tct gga tgg aat        288
Phe Val Phe Asn Gln Leu Trp Ser Arg Leu Gly Asp Ser Gly Trp Asn
                        85                  90                  95 gcg ttc atg gaa cat gtg gag gaa tta att gat act aaa ata gaa ggg        336
Ala Phe Met Glu His Val Glu Glu Leu Ile Asp Thr Lys Ile Glu Gly
            100                 105                 110 tat gca aaa aat aaa gcc tta tct gaa tta gca ggt ata caa aga aac        384
Tyr Ala Lys Asn Lys Ala Leu Ser Glu Leu Ala Gly Ile Gln Arg Asn
        115                 120                 125 ctt gaa aca tat ata caa tta cgt aat gaa tgg gaa aat gat att gaa        432
Leu Glu Thr Tyr Ile Gln Leu Arg Asn Glu Trp Glu Asn Asp Ile Glu
    130                 135                 140 aac tca aag gct caa ggt aag gta gct aat tac tat gaa agt ctt gag        480
Asn Ser Lys Ala Gln Gly Lys Val Ala Asn Tyr Tyr Glu Ser Leu Glu
145                 150                 155                 160 cag gcg gtt gaa agg agt atg cct caa ttt gca gtg gag aat ttt gaa        528
Gln Ala Val Glu Arg Ser Met Pro Gln Phe Ala Val Glu Asn Phe Glu
                165                 170                 175 gta cca ctt tta act gtc tat gtg caa gct gct aat ctt cat tta tta        576
Val Pro Leu Leu Thr Val Tyr Val Gln Ala Ala Asn Leu His Leu Leu
            180                 185                 190 tta tta aga gat gtt tca gtt tat gga aag tgt tgg gga tgg tcg gag        624
Leu Leu Arg Asp Val Ser Val Tyr Gly Lys Cys Trp Gly Trp Ser Glu
        195                 200                 205 cag aaa att aaa att tat tat gat aaa cag att aag tat acc cat gaa        672
Gln Lys Ile Lys Ile Tyr Tyr Asp Lys Gln Ile Lys Tyr Thr His Glu
    210                 215                 220 tac aca aat cat tgt gta aat tgg tat aat aaa gga ctt gag aga tta        720
Tyr Thr Asn His Cys Val Asn Trp Tyr Asn Lys Gly Leu Glu Arg Leu
225                 230                 235                 240 aaa aat aaa ggt tct tct tat caa gat tgg tac aat tat aat cgt ttc        768
Lys Asn Lys Gly Ser Ser Tyr Gln Asp Trp Tyr Asn Tyr Asn Arg Phe
                245                 250                 255 cgt aga gaa atg act ctt act gtt tta gat atc gtt gct tta ttc ccg        816
Arg Arg Glu Met Thr Leu Thr Val Leu Asp Ile Val Ala Leu Phe Pro
            260                 265                 270 cac tat gat gta caa act tat cca ata aca acc gtt gct cag cta aca        864
His Tyr Asp Val Gln Thr Tyr Pro Ile Thr Thr Val Ala Gln Leu Thr
        275                 280                 285 agg gaa gtt tat acg gat cct tta ctt aat ttt aat cct aaa tta cat        912
Arg Glu Val Tyr Thr Asp Pro Leu Leu Asn Phe Asn Pro Lys Leu His
    290                 295                 300 tct gtg tct caa tta cct agt ttt agt gac atg gaa aat gca aca att        960
Ser Val Ser Gln Leu Pro Ser Phe Ser Asp Met Glu Asn Ala Thr Ile
305                 310                 315                 320 aga act cca cat ctg atg gaa ttt tta aga atg cta aca att tat aca       1008
Arg Thr Pro His Leu Met Glu Phe Leu Arg Met Leu Thr Ile Tyr Thr
                325                 330                 335 gat tgg tat agt gtg gga aga aac tat tat tgg gga gga cat cgc gtg       1056
Asp Trp Tyr Ser Val Gly Arg Asn Tyr Tyr Trp Gly Gly His Arg Val
            340                 345                 350 acg tct tac cat gta gga gga gag aat ata aga tca cct cta tat ggt       1104
Thr Ser Tyr His Val Gly Gly Glu Asn Ile Arg Ser Pro Leu Tyr Gly
        355                 360                 365 aga gag gca aat caa gag gtt cct aga gat ttt tat ttt tat gga ccc       1152
Arg Glu Ala Asn Gln Glu Val Pro Arg Asp Phe Tyr Phe Tyr Gly Pro
    370                 375                 380 gtt ttt aag acg tta tca aag ccg act cta aga cca tta cag cag cct       1200
```

```
Val Phe Lys Thr Leu Ser Lys Pro Thr Leu Arg Pro Leu Gln Gln Pro
385                 390                 395                 400 gca cca gct cct cct ttt aat tta cgt agc tta gag gga gta gaa ttc    1248
Ala Pro Ala Pro Pro Phe Asn Leu Arg Ser Leu Glu Gly Val Glu Phe
                405                 410                 415 cac act cct aca ggt agt ttt atg tat cgt gaa aga gga tcg gta gat    1296
His Thr Pro Thr Gly Ser Phe Met Tyr Arg Glu Arg Gly Ser Val Asp
            420                 425                 430 tct ttt aat gag ttg ccg cct ttt aat cca gtt ggg tta cct cat aag    1344
Ser Phe Asn Glu Leu Pro Pro Phe Asn Pro Val Gly Leu Pro His Lys
        435                 440                 445 gta tac agt cac cgt tta tgt cat gca acg ttt gtt cgt aaa tct ggg    1392
Val Tyr Ser His Arg Leu Cys His Ala Thr Phe Val Arg Lys Ser Gly
    450                 455                 460 acc cct tat tta aca aca ggt gcc atc ttt tct tgg aca cat cgt agt    1440
Thr Pro Tyr Leu Thr Thr Gly Ala Ile Phe Ser Trp Thr His Arg Ser
465                 470                 475                 480 gct gaa gaa acc aat aca att gaa tca aat att att acg caa atc ccg    1488
Ala Glu Glu Thr Asn Thr Ile Glu Ser Asn Ile Ile Thr Gln Ile Pro
                485                 490                 495 tta gta aaa gca tat caa att ggg tca ggc act act gta agg aaa gga    1536
Leu Val Lys Ala Tyr Gln Ile Gly Ser Gly Thr Thr Val Arg Lys Gly
            500                 505                 510 cca gga ttc aca gga ggg gat ata ctt cga aga aca ggt cct gga aca    1584
Pro Gly Phe Thr Gly Gly Asp Ile Leu Arg Arg Thr Gly Pro Gly Thr
        515                 520                 525 ttt gga gat atg aga ata aat att aat gca cca tta tct caa aga tat    1632
Phe Gly Asp Met Arg Ile Asn Ile Asn Ala Pro Leu Ser Gln Arg Tyr
    530                 535                 540 cgt gta agg att cgt tat gct tct acg aca gat tta caa ttt gtc acg    1680
Arg Val Arg Ile Arg Tyr Ala Ser Thr Thr Asp Leu Gln Phe Val Thr
545                 550                 555                 560 agt att aat ggg acc acc att aat att ggt aac ttc ccg aaa act att    1728
Ser Ile Asn Gly Thr Thr Ile Asn Ile Gly Asn Phe Pro Lys Thr Ile
                565                 570                 575 aat aat cta aat act tta ggt tct gag ggc tat aga aca gta tcg ttt    1776
Asn Asn Leu Asn Thr Leu Gly Ser Glu Gly Tyr Arg Thr Val Ser Phe
            580                 585                 590 agt act cca ttt agt ttc tca aat gca caa agc ata ttt aga tta ggt    1824
Ser Thr Pro Phe Ser Phe Ser Asn Ala Gln Ser Ile Phe Arg Leu Gly
        595                 600                 605 ata caa gca ttt tct gga gtt caa gaa gtt tat gtg gat aaa att gaa    1872
Ile Gln Ala Phe Ser Gly Val Gln Glu Val Tyr Val Asp Lys Ile Glu
    610                 615                 620 ttt att cct gtt gaa tag                                            1890
Phe Ile Pro Val Glu *
625

<210> SEQ ID NO 3
<211> LENGTH: 629
<212> TYPE: PRT
<213> ORGANISM: Bacillus thuringiensis

<400> SEQUENCE: 3

Met Ser Glu Leu Lys Gly Lys Phe Lys Lys Ser Thr Asn Arg Thr Cys
1               5                   10                  15

Cys Leu Leu Lys Ile Ile Asn Ile Gly Gly Arg Gly Met Asn Ser Lys
            20                  25                  30

Glu His Asp Tyr Leu Lys Val Cys Asn Asp Leu Ser Asp Ala Asn Ile
        35                  40                  45
```

```
Asn Met Glu Arg Phe Asp Lys Asn Asp Ala Leu Glu Ile Gly Met Ser
    50                  55                  60

Ile Val Ser Glu Leu Ile Gly Met Ile Pro Gly Gly Thr Ala Leu Gln
65                  70                  75                  80

Phe Val Phe Asn Gln Leu Trp Ser Arg Leu Gly Asp Ser Gly Trp Asn
                85                  90                  95

Ala Phe Met Glu His Val Glu Glu Leu Ile Asp Thr Lys Ile Glu Gly
            100                 105                 110

Tyr Ala Lys Asn Lys Ala Leu Ser Glu Leu Ala Gly Ile Gln Arg Asn
        115                 120                 125

Leu Glu Thr Tyr Ile Gln Leu Arg Asn Glu Trp Glu Asn Asp Ile Glu
    130                 135                 140

Asn Ser Lys Ala Gln Gly Lys Val Ala Asn Tyr Tyr Glu Ser Leu Glu
145                 150                 155                 160

Gln Ala Val Glu Arg Ser Met Pro Gln Phe Ala Val Glu Asn Phe Glu
                165                 170                 175

Val Pro Leu Leu Thr Val Tyr Val Gln Ala Ala Asn Leu His Leu Leu
            180                 185                 190

Leu Leu Arg Asp Val Ser Val Tyr Gly Lys Cys Trp Gly Trp Ser Glu
        195                 200                 205

Gln Lys Ile Lys Ile Tyr Tyr Asp Lys Gln Ile Lys Tyr Thr His Glu
    210                 215                 220

Tyr Thr Asn His Cys Val Asn Trp Tyr Asn Lys Gly Leu Glu Arg Leu
225                 230                 235                 240

Lys Asn Lys Gly Ser Ser Tyr Gln Asp Trp Tyr Asn Tyr Asn Arg Phe
                245                 250                 255

Arg Arg Glu Met Thr Leu Thr Val Leu Asp Ile Val Ala Leu Phe Pro
            260                 265                 270

His Tyr Asp Val Gln Thr Tyr Pro Ile Thr Thr Val Ala Gln Leu Thr
        275                 280                 285

Arg Glu Val Tyr Thr Asp Pro Leu Leu Asn Phe Asn Pro Lys Leu His
    290                 295                 300

Ser Val Ser Gln Leu Pro Ser Phe Ser Asp Met Glu Asn Ala Thr Ile
305                 310                 315                 320

Arg Thr Pro His Leu Met Glu Phe Leu Arg Met Leu Thr Ile Tyr Thr
                325                 330                 335

Asp Trp Tyr Ser Val Gly Arg Asn Tyr Tyr Trp Gly Gly His Arg Val
            340                 345                 350

Thr Ser Tyr His Val Gly Gly Glu Asn Ile Arg Ser Pro Leu Tyr Gly
        355                 360                 365

Arg Glu Ala Asn Gln Glu Val Pro Arg Asp Phe Tyr Phe Tyr Gly Pro
    370                 375                 380

Val Phe Lys Thr Leu Ser Lys Pro Thr Leu Arg Pro Leu Gln Gln Pro
385                 390                 395                 400

Ala Pro Ala Pro Pro Phe Asn Leu Arg Ser Leu Glu Gly Val Glu Phe
                405                 410                 415

His Thr Pro Thr Gly Ser Phe Met Tyr Arg Glu Arg Gly Ser Val Asp
            420                 425                 430

Ser Phe Asn Glu Leu Pro Pro Phe Asn Pro Val Gly Leu Pro His Lys
        435                 440                 445

Val Tyr Ser His Arg Leu Cys His Ala Thr Phe Val Arg Lys Ser Gly
450                 455                 460
```

-continued

```
Thr Pro Tyr Leu Thr Thr Gly Ala Ile Phe Ser Trp Thr His Arg Ser
465                 470                 475                 480

Ala Glu Glu Thr Asn Thr Ile Glu Ser Asn Ile Ile Thr Gln Ile Pro
            485                 490                 495

Leu Val Lys Ala Tyr Gln Ile Gly Ser Gly Thr Thr Val Arg Lys Gly
        500                 505                 510

Pro Gly Phe Thr Gly Gly Asp Ile Leu Arg Arg Thr Gly Pro Gly Thr
    515                 520                 525

Phe Gly Asp Met Arg Ile Asn Ile Asn Ala Pro Leu Ser Gln Arg Tyr
530                 535                 540

Arg Val Arg Ile Arg Tyr Ala Ser Thr Thr Asp Leu Gln Phe Val Thr
545                 550                 555                 560

Ser Ile Asn Gly Thr Thr Ile Asn Ile Gly Asn Phe Pro Lys Thr Ile
                565                 570                 575

Asn Asn Leu Asn Thr Leu Gly Ser Glu Gly Tyr Arg Thr Val Ser Phe
            580                 585                 590

Ser Thr Pro Phe Ser Phe Ser Asn Ala Gln Ser Ile Phe Arg Leu Gly
        595                 600                 605

Ile Gln Ala Phe Ser Gly Val Gln Glu Val Tyr Val Asp Lys Ile Glu
    610                 615                 620

Phe Ile Pro Val Glu
625

<210> SEQ ID NO 4
<211> LENGTH: 1806
<212> TYPE: DNA
<213> ORGANISM: Bacillus thuringiensis
<220

-continued

| | | |
|---|---|---|
| gag aat ttt gaa gta cca ctt tta act gtc tat gtg caa gct gct aat<br>Glu Asn Phe Glu Val Pro Leu Leu Thr Val Tyr Val Gln Ala Ala Asn<br>145                    150                    155                    160 | 480 |
| ctt cat tta tta tta tta aga gat gtt tca gtt tat gga aag tgt tgg<br>Leu His Leu Leu Leu Leu Arg Asp Val Ser Val Tyr Gly Lys Cys Trp<br>                    165                    170                    175 | 528 |
| gga tgg tcg gag cag aaa att aaa att tat tat gat aaa cag att aag<br>Gly Trp Ser Glu Gln Lys Ile Lys Ile Tyr Tyr Asp Lys Gln Ile Lys<br>              180                    185                    190 | 576 |
| tat acc cat gaa tac aca aat cat tgt gta aat tgg tat aat aaa gga<br>Tyr Thr His Glu Tyr Thr Asn His Cys Val Asn Trp Tyr Asn Lys Gly<br>195                    200                    205 | 624 |
| ctt gag aga tta aaa aat aaa ggt tct tct tat caa gat tgg tac aat<br>Leu Glu Arg Leu Lys Asn Lys Gly Ser Ser Tyr Gln Asp Trp Tyr Asn<br>210                    215                    220 | 672 |
| tat aat cgt ttc cgt aga gaa atg act ctt act gtt tta gat atc gtt<br>Tyr Asn Arg Phe Arg Arg Glu Met Thr Leu Thr Val Leu Asp Ile Val<br>225                    230                    235                    240 | 720 |
| gct tta ttc ccg cac tat gat gta caa act tat cca ata aca acc gtt<br>Ala Leu Phe Pro His Tyr Asp Val Gln Thr Tyr Pro Ile Thr Thr Val<br>                    245                    250                    255 | 768 |
| gct cag cta aca agg gaa gtt tat acg gat cct tta ctt aat ttt aat<br>Ala Gln Leu Thr Arg Glu Val Tyr Thr Asp Pro Leu Leu Asn Phe Asn<br>                    260                    265                    270 | 816 |
| cct aaa tta cat tct gtg tct caa tta cct agt ttt agt gac atg gaa<br>Pro Lys Leu His Ser Val Ser Gln Leu Pro Ser Phe Ser Asp Met Glu<br>275                    280                    285 | 864 |
| aat gca aca att aga act cca cat ctg atg gaa ttt tta aga atg cta<br>Asn Ala Thr Ile Arg Thr Pro His Leu Met Glu Phe Leu Arg Met Leu<br>290                    295                    300 | 912 |
| aca att tat aca gat tgg tat agt gtg gga aga aac tat tat tgg gga<br>Thr Ile Tyr Thr Asp Trp Tyr Ser Val Gly Arg Asn Tyr Tyr Trp Gly<br>305                    310                    315                    320 | 960 |
| gga cat cgc gtg acg tct tac cat gta gga gga gag aat ata aga tca<br>Gly His Arg Val Thr Ser Tyr His Val Gly Gly Glu Asn Ile Arg Ser<br>                    325                    330                    335 | 1008 |
| cct cta tat ggt aga gag gca aat caa gag gtt cct aga gat ttt tat<br>Pro Leu Tyr Gly Arg Glu Ala Asn Gln Glu Val Pro Arg Asp Phe Tyr<br>                    340                    345                    350 | 1056 |
| ttt tat gga ccc gtt ttt aag acg tta tca aag ccg act cta aga cca<br>Phe Tyr Gly Pro Val Phe Lys Thr Leu Ser Lys Pro Thr Leu Arg Pro<br>              355                    360                    365 | 1104 |
| tta cag cag cct gca cca gct cct cct ttt aat tta cgt agc tta gag<br>Leu Gln Gln Pro Ala Pro Ala Pro Pro Phe Asn Leu Arg Ser Leu Glu<br>370                    375                    380 | 1152 |
| gga gta gaa ttc cac act cct aca ggt agt ttt atg tat cgt gaa aga<br>Gly Val Glu Phe His Thr Pro Thr Gly Ser Phe Met Tyr Arg Glu Arg<br>385                    390                    395                    400 | 1200 |
| gga tcg gta gat tct ttt aat gag ttg ccg cct ttt aat cca gtt ggg<br>Gly Ser Val Asp Ser Phe Asn Glu Leu Pro Pro Phe Asn Pro Val Gly<br>                    405                    410                    415 | 1248 |
| tta cct cat aag gta tac agt cac cgt tta tgt cat gca acg ttt gtt<br>Leu Pro His Lys Val Tyr Ser His Arg Leu Cys His Ala Thr Phe Val<br>                    420                    425                    430 | 1296 |
| cgt aaa tct ggg acc cct tat tta aca aca ggt gcc atc ttt tct tgg<br>Arg Lys Ser Gly Thr Pro Tyr Leu Thr Thr Gly Ala Ile Phe Ser Trp<br>              435                    440                    445 | 1344 |
| aca cat cgt agt gct gaa gaa acc aat aca att gaa tca aat att att<br>Thr His Arg Ser Ala Glu Glu Thr Asn Thr Ile Glu Ser Asn Ile Ile | 1392 |

-continued

```
            450                 455                 460
acg caa atc ccg tta gta aaa gca tat caa att ggg tca ggc act act      1440
Thr Gln Ile Pro Leu Val Lys Ala Tyr Gln Ile Gly Ser Gly Thr Thr
465                 470                 475                 480 gta agg aaa gga cca gga ttc aca gga ggg gat ata ctt cga aga aca      1488
Val Arg Lys Gly Pro Gly Phe Thr Gly Gly Asp Ile Leu Arg Arg Thr
                485                 490                 495 ggt cct gga aca ttt gga gat atg aga ata aat att aat gca cca tta      1536
Gly Pro Gly Thr Phe Gly Asp Met Arg Ile Asn Ile Asn Ala Pro Leu
            500                 505                 510 tct caa aga tat cgt gta agg att cgt tat gct tct acg aca gat tta      1584
Ser Gln Arg Tyr Arg Val Arg Ile Arg Tyr Ala Ser Thr Thr Asp Leu
        515                 520                 525 caa ttt gtc acg agt att aat ggg acc acc att aat att ggt aac ttc      1632
Gln Phe Val Thr Ser Ile Asn Gly Thr Thr Ile Asn Ile Gly Asn Phe
    530                 535                 540 ccg aaa act att aat aat cta aat act tta ggt tct gag ggc tat aga      1680
Pro Lys Thr Ile Asn Asn Leu Asn Thr Leu Gly Ser Glu Gly Tyr Arg
545                 550                 555                 560 aca gta tcg ttt agt act cca ttt agt ttc tca aat gca caa agc ata      1728
Thr Val Ser Phe Ser Thr Pro Phe Ser Phe Ser Asn Ala Gln Ser Ile
                565                 570                 575 ttt aga tta ggt ata caa gca ttt tct gga gtt caa gaa gtt tat gtg      1776
Phe Arg Leu Gly Ile Gln Ala Phe Ser Gly Val Gln Glu Val Tyr Val
            580                 585                 590 gat aaa att gaa ttt att cct gtt gaa tag                              1806
Asp Lys Ile Glu Phe Ile Pro Val Glu *
        595                 600

<210> SEQ ID NO 5
<211> LENGTH: 601
<212> TYPE: PRT
<213> ORGANISM: Bacillus thuringiensis

<400> SEQUENCE: 5

Met Asn Ser Lys Glu His Asp Tyr Leu Lys Val Cys Asn Asp Leu Ser
 1               5                  10                  15

Asp Ala Asn Ile Asn Met Glu Arg Phe Asp Lys Asn Asp Ala Leu Glu
            20                  25                  30

Ile Gly Met Ser Ile Val Ser Glu Leu Ile Gly Met Ile Pro Gly Gly
        35                  40                  45

Thr Ala Leu Gln Phe Val Phe Asn Gln Leu Trp Ser Arg Leu Gly Asp
    50                  55                  60

Ser Gly Trp Asn Ala Phe Met Glu His Val Glu Glu Leu Ile Asp Thr
65                  70                  75                  80

Lys Ile Glu Gly Tyr Ala Lys Asn Lys Ala Leu Ser Glu Leu Ala Gly
                85                  90                  95

Ile Gln Arg Asn Leu Glu Thr Tyr Ile Gln Leu Arg Asn Glu Trp Glu
            100                 105                 110

Asn Asp Ile Glu Asn Ser Lys Ala Gln Gly Lys Val Ala Asn Tyr Tyr
        115                 120                 125

Glu Ser Leu Glu Gln Ala Val Glu Arg Ser Met Pro Gln Phe Ala Val
    130                 135                 140

Glu Asn Phe Glu Val Pro Leu Leu Thr Val Tyr Val Gln Ala Ala Asn
145                 150                 155                 160

Leu His Leu Leu Leu Leu Arg Asp Val Ser Val Tyr Gly Lys Cys Trp
                165                 170                 175
```

-continued

```
Gly Trp Ser Glu Gln Lys Ile Lys Ile Tyr Tyr Asp Lys Gln Ile Lys
                180                 185                 190

Tyr Thr His Glu Tyr Thr Asn His Cys Val Asn Trp Tyr Asn Lys Gly
            195                 200                 205

Leu Glu Arg Leu Lys Asn Lys Gly Ser Ser Tyr Gln Asp Trp Tyr Asn
        210                 215                 220

Tyr Asn Arg Phe Arg Arg Glu Met Thr Leu Thr Val Leu Asp Ile Val
225                 230                 235                 240

Ala Leu Phe Pro His Tyr Asp Val Gln Thr Tyr Pro Ile Thr Thr Val
                245                 250                 255

Ala Gln Leu Thr Arg Glu Val Tyr Thr Asp Pro Leu Leu Asn Phe Asn
            260                 265                 270

Pro Lys Leu His Ser Val Ser Gln Leu Pro Ser Phe Ser Asp Met Glu
        275                 280                 285

Asn Ala Thr Ile Arg Thr Pro His Leu Met Glu Phe Leu Arg Met Leu
    290                 295                 300

Thr Ile Tyr Thr Asp Trp Tyr Ser Val Gly Arg Asn Tyr Tyr Trp Gly
305                 310                 315                 320

Gly His Arg Val Thr Ser Tyr His Val Gly Gly Glu Asn Ile Arg Ser
                325                 330                 335

Pro Leu Tyr Gly Arg Glu Ala Asn Gln Glu Val Pro Arg Asp Phe Tyr
            340                 345                 350

Phe Tyr Gly Pro Val Phe Lys Thr Leu Ser Lys Pro Thr Leu Arg Pro
        355                 360                 365

Leu Gln Gln Pro Ala Pro Ala Pro Pro Phe Asn Leu Arg Ser Leu Glu
    370                 375                 380

Gly Val Glu Phe His Thr Pro Thr Gly Ser Phe Met Tyr Arg Glu Arg
385                 390                 395                 400

Gly Ser Val Asp Ser Phe Asn Glu Leu Pro Pro Phe Asn Pro Val Gly
                405                 410                 415

Leu Pro His Lys Val Tyr Ser His Arg Leu Cys His Ala Thr Phe Val
            420                 425                 430

Arg Lys Ser Gly Thr Pro Tyr Leu Thr Thr Gly Ala Ile Phe Ser Trp
        435                 440                 445

Thr His Arg Ser Ala Glu Glu Thr Asn Thr Ile Glu Ser Asn Ile Ile
    450                 455                 460

Thr Gln Ile Pro Leu Val Lys Ala Tyr Gln Ile Gly Ser Gly Thr Thr
465                 470                 475                 480

Val Arg Lys Gly Pro Gly Phe Thr Gly Gly Asp Ile Leu Arg Arg Thr
                485                 490                 495

Gly Pro Gly Thr Phe Gly Asp Met Arg Ile Asn Ile Asn Ala Pro Leu
            500                 505                 510

Ser Gln Arg Tyr Arg Val Arg Ile Arg Tyr Ala Ser Thr Thr Asp Leu
        515                 520                 525

Gln Phe Val Thr Ser Ile Asn Gly Thr Thr Ile Asn Ile Gly Asn Phe
    530                 535                 540

Pro Lys Thr Ile Asn Asn Leu Asn Thr Leu Gly Ser Glu Gly Tyr Arg
545                 550                 555                 560

Thr Val Ser Phe Ser Thr Pro Phe Ser Phe Ser Asn Ala Gln Ser Ile
                565                 570                 575

Phe Arg Leu Gly Ile Gln Ala Phe Ser Gly Val Gln Glu Val Tyr Val
            580                 585                 590

Asp Lys Ile Glu Phe Ile Pro Val Glu
```

-continued

```
                 595                 600

<210> SEQ ID NO 6
<211> LENGTH: 1178
<212> TYPE: PRT
<213> ORGANISM: Bacillus thuringiensis

<400> SEQUENCE: 6

Met Asp Asn Asn Pro Asn Ile Asn Glu Cys Ile Pro Tyr Asn Cys Leu
 1               5                  10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Thr
    290                 295                 300

Ile Tyr Thr Asp Ala His Arg Gly Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365
```

```
Arg Pro Phe Asn Ile Gly Ile Asn Asn Gln Gln Leu Ser Val Leu Asp
    370                 375                 380
Gly Thr Glu Phe Ala Tyr Gly Thr Ser Ser Asn Leu Pro Ser Ala Val
385                     390                 395                 400
Tyr Arg Lys Ser Gly Thr Val Asp Ser Leu Asp Glu Ile Pro Pro Gln
                405                 410                 415
Asn Asn Asn Val Pro Pro Arg Gln Gly Phe Ser His Arg Leu Ser His
            420                 425                 430
Val Ser Met Phe Arg Ser Gly Phe Ser Asn Ser Val Ser Ile Ile
            435                 440                 445
Arg Ala Pro Met Phe Ser Trp Ile His Arg Ser Ala Glu Phe Asn Asn
450                 455                 460
Ile Ile Ala Ser Asp Ser Ile Thr Gln Ile Pro Ala Val Lys Gly Asn
465                 470                 475                 480
Phe Leu Phe Asn Gly Ser Val Ile Ser Gly Pro Gly Phe Thr Gly Gly
                485                 490                 495
Asp Leu Val Arg Leu Asn Ser Ser Gly Asn Asn Ile Gln Asn Arg Gly
                500                 505                 510
Tyr Ile Glu Val Pro Ile His Phe Pro Ser Thr Ser Arg Tyr Arg
            515                 520                 525
Val Arg Val Arg Tyr Ala Ser Val Thr Pro Ile His Leu Asn Val Asn
530                 535                 540
Trp Gly Asn Ser Ser Ile Phe Ser Asn Thr Val Pro Ala Thr Ala Thr
545                 550                 555                 560
Ser Leu Asp Asn Leu Gln Ser Ser Asp Phe Gly Tyr Phe Glu Ser Ala
                565                 570                 575
Asn Ala Phe Thr Ser Ser Leu Gly Asn Ile Val Gly Val Arg Asn Phe
                580                 585                 590
Ser Gly Thr Ala Gly Val Ile Ile Asp Arg Phe Glu Phe Ile Pro Val
            595                 600                 605
Thr Ala Thr Leu Glu Ala Glu Tyr Asn Leu Glu Arg Ala Gln Lys Ala
            610                 615                 620
Val Asn Ala Leu Phe Thr Ser Thr Asn Gln Leu Gly Leu Lys Thr Asn
625                 630                 635                 640
Val Thr Asp Tyr His Ile Asp Gln Val Ser Asn Leu Val Thr Tyr Leu
                645                 650                 655
Ser Asp Glu Phe Cys Leu Asp Glu Lys Arg Glu Leu Ser Glu Lys Val
                660                 665                 670
Lys His Ala Lys Arg Leu Ser Asp Glu Arg Asn Leu Leu Gln Asp Ser
            675                 680                 685
Asn Phe Lys Asp Ile Asn Arg Gln Pro Glu Arg Gly Trp Gly Gly Ser
            690                 695                 700
Thr Gly Ile Thr Ile Gln Gly Gly Asp Asp Val Phe Lys Glu Asn Tyr
705                 710                 715                 720
Val Thr Leu Ser Gly Thr Phe Asp Glu Cys Tyr Pro Thr Tyr Leu Tyr
                725                 730                 735
Gln Lys Ile Asp Glu Ser Lys Leu Lys Ala Phe Thr Arg Tyr Gln Leu
            740                 745                 750
Arg Gly Tyr Ile Glu Asp Ser Gln Asp Leu Glu Ile Tyr Leu Ile Arg
            755                 760                 765
Tyr Asn Ala Lys His Glu Thr Val Asn Val Pro Gly Thr Gly Ser Leu
            770                 775                 780
Trp Pro Leu Ser Ala Gln Ser Pro Ile Gly Lys Cys Gly Glu Pro Asn
```

```
                785                 790                 795                 800
Arg Cys Ala Pro His Leu Glu Trp Asn Pro Asp Leu Asp Cys Ser Cys
            805                 810                 815
Arg Asp Gly Glu Lys Cys Ala His His Ser His His Phe Ser Leu Asp
            820                 825                 830
Ile Asp Val Gly Cys Thr Asp Leu Asn Glu Asp Leu Gly Val Trp Val
            835                 840                 845
Ile Phe Lys Ile Lys Thr Gln Asp Gly His Ala Arg Leu Gly Asn Leu
        850                 855                 860
Glu Phe Leu Glu Glu Lys Pro Leu Val Gly Glu Ala Leu Ala Arg Val
865                 870                 875                 880
Lys Arg Ala Glu Lys Lys Trp Arg Asp Lys Arg Glu Lys Leu Glu Trp
                885                 890                 895
Glu Thr Asn Ile Val Tyr Lys Glu Ala Lys Glu Ser Val Asp Ala Leu
            900                 905                 910
Phe Val Asn Ser Gln Tyr Asp Gln Leu Gln Ala Asp Thr Asn Ile Ala
        915                 920                 925
Met Ile His Ala Ala Asp Lys Arg Val His Ser Ile Arg Glu Ala Tyr
    930                 935                 940
Leu Pro Glu Leu Ser Val Ile Pro Gly Val Asn Ala Ala Ile Phe Glu
945                 950                 955                 960
Glu Leu Glu Gly Arg Ile Phe Thr Ala Phe Ser Leu Tyr Asp Ala Arg
                965                 970                 975
Asn Val Ile Lys Asn Gly Asp Phe Asn Asn Gly Leu Ser Cys Trp Asn
            980                 985                 990
Val Lys Gly His Val Asp Val Glu Glu Gln Asn Asn Gln Arg Ser Val
        995                 1000                1005
Leu Val Val Pro Glu Trp Glu Ala Glu Val Ser Gln Glu Val Arg Val
    1010                1015                1020
Cys Pro Gly Arg Gly Tyr Ile Leu Arg Val Thr Ala Tyr Lys Glu Gly
1025                1030                1035                1040
Tyr Gly Glu Gly Cys Val Thr Ile His Glu Ile Glu Asn Asn Thr Asp
                1045                1050                1055
Glu Leu Lys Phe Ser Asn Cys Val Glu Glu Ile Tyr Pro Asn Asn
            1060                1065                1070
Thr Val Thr Cys Asn Asp Tyr Thr Val Asn Gln Glu Glu Tyr Gly Gly
        1075                1080                1085
Ala Tyr Thr Ser Arg Asn Arg Gly Tyr Asn Glu Ala Pro Ser Val Pro
    1090                1095                1100
Ala Asp Tyr Ala Ser Val Tyr Glu Glu Lys Ser Tyr Thr Asp Gly Arg
1105                1110                1115                1120
Arg Glu Asn Pro Cys Glu Phe Asn Arg Gly Tyr Arg Asp Tyr Thr Pro
                1125                1130                1135
Leu Pro Val Gly Tyr Val Thr Lys Glu Leu Glu Tyr Phe Pro Glu Thr
            1140                1145                1150
Asp Lys Val Trp Ile Glu Ile Gly Glu Thr Glu Gly Thr Phe Ile Val
        1155                1160                1165
Asp Ser Val Glu Leu Leu Leu Met Glu Glu
    1170                1175

<210> SEQ ID NO 7
<211> LENGTH: 1189
<212> TYPE: PRT
<213> ORGANISM: Bacillus thuringiensis
```

<400> SEQUENCE: 7

```
Met Glu Glu Asn Asn Gln Asn Gln Cys Ile Pro Tyr Asn Cys Leu Ser
1               5                   10                  15

Asn Pro Glu Glu Val Leu Leu Asp Gly Glu Arg Ile Ser Thr Gly Asn
            20                  25                  30

Ser Ser Ile Asp Ile Ser Leu Ser Leu Val Gln Phe Leu Val Ser Asn
        35                  40                  45

Phe Val Pro Gly Gly Gly Phe Leu Val Gly Leu Ile Asp Phe Val Trp
    50                  55                  60

Gly Ile Val Gly Pro Ser Gln Trp Asp Ala Phe Leu Val Gln Ile Glu
65                  70                  75                  80

Gln Leu Ile Asn Glu Arg Ile Ala Glu Phe Ala Arg Asn Ala Ala Ile
                85                  90                  95

Ala Asn Leu Glu Gly Leu Gly Asn Asn Phe Asn Ile Tyr Val Glu Ala
            100                 105                 110

Phe Lys Glu Trp Glu Glu Asp Pro Asn Asn Pro Ala Thr Arg Thr Arg
        115                 120                 125

Val Ile Asp Arg Phe Arg Ile Leu Asp Gly Leu Leu Glu Arg Asp Ile
    130                 135                 140

Pro Ser Phe Arg Ile Ser Gly Phe Glu Val Pro Leu Leu Ser Val Tyr
145                 150                 155                 160

Ala Gln Ala Ala Asn Leu His Leu Ala Ile Leu Arg Asp Ser Val Ile
                165                 170                 175

Phe Gly Glu Arg Trp Gly Leu Thr Thr Ile Asn Val Asn Glu Asn Tyr
            180                 185                 190

Asn Arg Leu Ile Arg His Ile Asp Glu Tyr Ala Asp His Cys Ala Asn
        195                 200                 205

Thr Tyr Asn Arg Gly Leu Asn Asn Leu Pro Lys Ser Thr Tyr Gln Asp
    210                 215                 220

Trp Ile Thr Tyr Asn Arg Leu Arg Arg Asp Leu Thr Leu Thr Val Leu
225                 230                 235                 240

Asp Ile Ala Ala Phe Phe Pro Asn Tyr Asp Asn Arg Arg Tyr Pro Ile
                245                 250                 255

Gln Pro Val Gly Gln Leu Thr Arg Glu Val Tyr Thr Asp Pro Leu Ile
            260                 265                 270

Asn Phe Asn Pro Gln Leu Gln Ser Val Ala Gln Leu Pro Thr Phe Asn
        275                 280                 285

Val Met Glu Ser Ser Ala Ile Arg Asn Pro His Leu Phe Asp Ile Leu
    290                 295                 300

Asn Asn Leu Thr Ile Phe Thr Asp Trp Phe Ser Val Gly Arg Asn Phe
305                 310                 315                 320

Tyr Trp Gly Gly His Arg Val Ile Ser Ser Leu Ile Gly Gly Gly Asn
                325                 330                 335

Ile Thr Ser Pro Ile Tyr Gly Arg Glu Ala Asn Gln Glu Pro Pro Arg
            340                 345                 350

Ser Phe Thr Phe Asn Gly Pro Val Phe Arg Thr Leu Ser Asn Pro Thr
        355                 360                 365

Leu Arg Leu Leu Gln Gln Pro Trp Pro Ala Pro Pro Phe Asn Leu Arg
    370                 375                 380

Gly Val Glu Gly Val Glu Phe Ser Thr Pro Thr Asn Ser Phe Thr Tyr
385                 390                 395                 400

Arg Gly Arg Gly Thr Val Asp Ser Leu Thr Glu Leu Pro Pro Glu Asp
```

```
                405                 410                 415
Asn Ser Val Pro Pro Arg Glu Gly Tyr Ser His Arg Leu Cys His Ala
            420                 425                 430

Thr Phe Val Gln Arg Ser Gly Thr Pro Phe Leu Thr Thr Gly Val Val
            435                 440                 445

Phe Ser Trp Thr His Arg Ser Ala Thr Leu Thr Asn Thr Ile Asp Pro
            450                 455                 460

Glu Arg Ile Asn Gln Ile Pro Leu Val Lys Gly Phe Arg Val Trp Gly
465                 470                 475                 480

Gly Thr Ser Val Ile Thr Gly Pro Gly Phe Thr Gly Gly Asp Ile Leu
                485                 490                 495

Arg Arg Asn Thr Phe Gly Asp Phe Val Ser Leu Gln Val Asn Ile Asn
            500                 505                 510

Ser Pro Ile Thr Gln Arg Tyr Arg Leu Arg Phe Arg Tyr Ala Ser Ser
            515                 520                 525

Arg Asp Ala Arg Val Ile Val Leu Thr Gly Ala Ala Ser Thr Gly Val
            530                 535                 540

Gly Gly Gln Val Ser Val Asn Met Pro Leu Gln Lys Thr Met Glu Ile
545                 550                 555                 560

Gly Glu Asn Leu Thr Ser Arg Thr Phe Arg Tyr Thr Asp Phe Ser Asn
                565                 570                 575

Pro Phe Ser Phe Arg Ala Asn Pro Asp Ile Ile Gly Ile Ser Glu Gln
            580                 585                 590

Pro Leu Phe Gly Ala Gly Ser Ile Ser Ser Gly Glu Leu Tyr Ile Asp
            595                 600                 605

Lys Ile Glu Ile Ile Leu Ala Asp Ala Thr Phe Glu Ala Glu Ser Asp
610                 615                 620

Leu Glu Arg Ala Gln Lys Ala Val Asn Ala Leu Phe Thr Ser Ser Asn
625                 630                 635                 640

Gln Ile Gly Leu Lys Thr Asp Val Thr Asp Tyr His Ile Asp Gln Val
                645                 650                 655

Ser Asn Leu Val Asp Cys Leu Ser Asp Glu Phe Cys Leu Asp Glu Lys
            660                 665                 670

Arg Glu Leu Ser Glu Lys Val Lys His Ala Lys Arg Leu Ser Asp Glu
            675                 680                 685

Arg Asn Leu Leu Gln Asp Pro Asn Phe Arg Gly Ile Asn Arg Gln Pro
            690                 695                 700

Asp Arg Gly Trp Arg Gly Ser Thr Asp Ile Thr Ile Gln Gly Gly Asp
705                 710                 715                 720

Asp Val Phe Lys Glu Asn Tyr Val Thr Leu Pro Gly Thr Val Asp Glu
                725                 730                 735

Cys Tyr Pro Thr Tyr Leu Tyr Gln Lys Ile Asp Glu Ser Lys Leu Lys
            740                 745                 750

Ala Tyr Thr Arg Tyr Glu Leu Arg Gly Tyr Ile Glu Asp Ser Gln Asp
            755                 760                 765

Leu Glu Ile Tyr Leu Ile Arg Tyr Asn Ala Lys His Glu Ile Val Asn
770                 775                 780

Val Pro Gly Thr Gly Ser Leu Trp Pro Leu Ser Ala Gln Ser Pro Ile
785                 790                 795                 800

Gly Lys Cys Gly Glu Pro Asn Arg Cys Ala Pro His Leu Glu Trp Asn
                805                 810                 815

Pro Asp Leu Asp Cys Ser Cys Arg Asp Gly Glu Lys Cys Ala His His
            820                 825                 830
```

```
Ser His His Phe Thr Leu Asp Ile Asp Val Gly Cys Thr Asp Leu Asn
            835                 840                 845

Glu Asp Leu Gly Val Trp Val Ile Phe Lys Ile Lys Thr Gln Asp Gly
850                 855                 860

His Ala Arg Leu Gly Asn Leu Glu Phe Leu Glu Glu Lys Pro Leu Leu
865                 870                 875                 880

Gly Glu Ala Leu Ala Arg Val Lys Arg Ala Glu Lys Lys Trp Arg Asp
            885                 890                 895

Lys Arg Glu Lys Leu Gln Leu Glu Thr Asn Ile Val Tyr Lys Glu Ala
            900                 905                 910

Lys Glu Ser Val Asp Ala Leu Phe Val Asn Ser Gln Tyr Asp Arg Leu
            915                 920                 925

Gln Val Asp Thr Asn Ile Ala Met Ile His Ala Ala Asp Lys Arg Val
            930                 935                 940

His Arg Ile Arg Glu Ala Tyr Leu Pro Glu Leu Ser Val Ile Pro Gly
945                 950                 955                 960

Val Asn Ala Ala Ile Phe Glu Glu Leu Glu Gly Arg Ile Phe Thr Ala
                965                 970                 975

Tyr Ser Leu Tyr Asp Ala Arg Asn Val Ile Lys Asn Gly Asp Phe Asn
            980                 985                 990

Asn Gly Leu Leu Cys Trp Asn Val Lys Gly His Val Asp Val Glu Glu
            995                 1000                1005

Gln Asn Asn His Arg Ser Val Leu Val Ile Pro Glu Trp Glu Ala Glu
    1010                1015                1020

Val Ser Gln Glu Val Arg Val Cys Pro Gly Arg Gly Tyr Ile Leu Arg
1025                1030                1035                1040

Val Thr Ala Tyr Lys Glu Gly Tyr Gly Glu Gly Cys Val Thr Ile His
                1045                1050                1055

Glu Ile Glu Asp Asn Thr Asp Glu Leu Lys Phe Ser Asn Cys Val Glu
            1060                1065                1070

Glu Glu Val Tyr Pro Asn Asn Thr Val Thr Cys Asn Asn Tyr Thr Gly
            1075                1080                1085

Thr Gln Glu Glu Tyr Glu Gly Thr Tyr Thr Ser Arg Asn Gln Gly Tyr
    1090                1095                1100

Asp Glu Ala Tyr Gly Asn Asn Pro Ser Val Pro Ala Asp Tyr Ala Ser
1105                1110                1115                1120

Val Tyr Glu Glu Lys Ser Tyr Thr Asp Gly Arg Arg Glu Asn Pro Cys
                1125                1130                1135

Glu Ser Asn Arg Gly Tyr Gly Asp Tyr Thr Pro Leu Pro Ala Gly Tyr
            1140                1145                1150

Val Thr Lys Asp Leu Glu Tyr Phe Pro Glu Thr Asp Lys Val Trp Ile
            1155                1160                1165

Glu Ile Gly Glu Thr Glu Gly Thr Phe Ile Val Asp Ser Val Glu Leu
            1170                1175                1180

Leu Leu Met Glu Glu
1185

<210> SEQ ID NO 8
<211> LENGTH: 633
<212> TYPE: PRT
<213> ORGANISM: Bacillus thuringiensis

<400> SEQUENCE: 8

Met Asn Asn Val Leu Asn Ser Gly Arg Thr Thr Ile Cys Asp Ala Tyr
```

-continued

```
  1               5                   10                  15
Asn Val Val Ala His Asp Pro Phe Ser Phe Glu His Lys Ser Leu Asp
                 20                  25                  30

Thr Ile Gln Lys Glu Trp Met Glu Trp Lys Arg Thr Asp His Ser Leu
             35                  40                  45

Tyr Val Ala Pro Val Val Gly Thr Val Ser Ser Phe Leu Leu Lys Lys
             50                  55                  60

Val Gly Ser Leu Ile Gly Lys Arg Ile Leu Ser Glu Leu Trp Gly Ile
 65                  70                  75                  80

Ile Phe Pro Ser Gly Ser Thr Asn Leu Met Gln Asp Ile Leu Arg Glu
                 85                  90                  95

Thr Glu Gln Phe Leu Asn Gln Arg Leu Asn Thr Asp Thr Leu Ala Arg
                100                 105                 110

Val Asn Ala Glu Leu Ile Gly Leu Gln Ala Asn Ile Arg Glu Phe Asn
                115                 120                 125

Gln Gln Val Asp Asn Phe Leu Asn Pro Thr Gln Asn Pro Val Pro Leu
            130                 135                 140

Ser Ile Thr Ser Ser Val Asn Thr Met Gln Gln Leu Phe Leu Asn Arg
145                 150                 155                 160

Leu Pro Gln Phe Gln Ile Gln Gly Tyr Gln Leu Leu Leu Pro Leu
                165                 170                 175

Phe Ala Gln Ala Ala Asn Met His Leu Ser Phe Ile Arg Asp Val Ile
                180                 185                 190

Leu Asn Ala Asp Glu Trp Gly Ile Ser Ala Ala Thr Leu Arg Thr Tyr
            195                 200                 205

Arg Asp Tyr Leu Arg Asn Tyr Thr Arg Asp Tyr Ser Asn Tyr Cys Ile
    210                 215                 220

Asn Thr Tyr Gln Thr Ala Phe Arg Gly Leu Asn Thr Arg Leu His Asp
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Met Val Ser Ser Gly
                260                 265                 270

Ala Asn Leu Tyr Ala Ser Gly Ser Gly Pro Gln Gln Thr Gln Ser Phe
            275                 280                 285

Thr Ala Gln Asn Trp Pro Phe Leu Tyr Ser Leu Phe Gln Val Asn Ser
            290                 295                 300

Asn Tyr Ile Leu Ser Gly Ile Ser Gly Thr Arg Leu Ser Ile Thr Phe
305                 310                 315                 320

Pro Asn Ile Gly Gly Leu Pro Gly Ser Thr Thr Thr His Ser Leu Asn
                325                 330                 335

Ser Ala Arg Val Asn Tyr Ser Gly Gly Val Ser Ser Gly Leu Ile Gly
            340                 345                 350

Ala Thr Asn Leu Asn His Asn Phe Asn Cys Ser Thr Val Leu Pro Pro
            355                 360                 365

Leu Ser Thr Pro Phe Val Arg Ser Trp Leu Asp Ser Gly Thr Asp Arg
    370                 375                 380

Glu Gly Val Ala Thr Ser Thr Asn Trp Gln Thr Glu Ser Phe Gln Thr
385                 390                 395                 400

Thr Leu Ser Leu Arg Cys Gly Ala Phe Ser Ala Arg Gly Asn Ser Asn
                405                 410                 415

Tyr Phe Pro Asp Tyr Phe Ile Arg Asn Ile Ser Gly Val Pro Leu Val
            420                 425                 430
```

Ile Arg Asn Glu Asp Leu Thr Arg Pro Leu His Tyr Asn Gln Ile Arg
            435                 440                 445

Asn Ile Glu Ser Pro Ser Gly Thr Pro Gly Gly Ala Arg Ala Tyr Leu
        450                 455                 460

Val Ser Val His Asn Arg Lys Asn Asn Ile Tyr Ala Ala Asn Glu Asn
465                 470                 475                 480

Gly Thr Met Ile His Leu Ala Pro Glu Asp Tyr Thr Gly Phe Thr Ile
                485                 490                 495

Ser Pro Ile His Ala Thr Gln Val Asn Asn Gln Thr Arg Thr Phe Ile
                500                 505                 510

Ser Glu Lys Phe Gly Asn Gln Gly Asp Ser Leu Arg Phe Glu Gln Ser
            515                 520                 525

Asn Thr Thr Ala Arg Tyr Thr Leu Arg Gly Asn Gly Asn Ser Tyr Asn
        530                 535                 540

Leu Tyr Leu Arg Val Ser Ser Ile Gly Asn Ser Thr Ile Arg Val Thr
545                 550                 555                 560

Ile Asn Gly Arg Val Tyr Thr Val Ser Asn Val Asn Thr Thr Thr Asn
                565                 570                 575

Asn Asp Gly Val Asn Asp Asn Gly Ala Arg Phe Ser Asp Ile Asn Ile
                580                 585                 590

Gly Asn Ile Val Ala Ser Asp Asn Thr Asn Val Thr Leu Asp Ile Asn
            595                 600                 605

Val Thr Leu Asn Ser Gly Thr Pro Phe Asp Leu Met Asn Ile Met Phe
        610                 615                 620

Val Pro Thr Asn Leu Pro Pro Leu Tyr
625                 630

<210> SEQ ID NO 9
<211> LENGTH: 652
<212> TYPE: PRT
<213> ORGANISM: Bacillus thuringiensis

<400> SEQUENCE: 9

Met Ile Arg Lys Gly Gly Arg Lys Met Asn Pro Asn Asn Arg Ser Glu
  1               5                  10                  15

His Asp Thr Ile Lys Thr Thr Glu Asn Asn Glu Val Pro Thr Asn His
                20                  25                  30

Val Gln Tyr Pro Leu Ala Glu Thr Pro Asn Pro Thr Leu Glu Asp Leu
            35                  40                  45

Asn Tyr Lys Glu Phe Leu Arg Met Thr Ala Asp Asn Asn Thr Glu Ala
        50                  55                  60

Leu Asp Ser Ser Thr Thr Lys Asp Val Ile Gln Lys Gly Ile Ser Val
65                  70                  75                  80

Val Gly Asp Leu Leu Gly Val Val Gly Phe Pro Phe Gly Gly Ala Leu
                85                  90                  95

Val Ser Phe Tyr Thr Asn Phe Leu Asn Thr Ile Trp Pro Ser Glu Asp
            100                 105                 110

Pro Trp Lys Ala Phe Met Glu Gln Val Glu Ala Leu Met Asp Gln Lys
        115                 120                 125

Ile Ala Asp Tyr Ala Lys Asn Lys Ala Leu Ala Glu Leu Gln Gly Leu
    130                 135                 140

Gln Asn Asn Val Glu Asp Tyr Val Ser Ala Leu Ser Ser Trp Gln Lys
145                 150                 155                 160

Asn Pro Val Ser Ser Arg Asn Pro His Ser Gln Gly Arg Ile Arg Glu

```
                165                 170                 175
Leu Phe Ser Gln Ala Glu Ser His Phe Arg Asn Ser Met Pro Ser Phe
                180                 185                 190
Ala Ile Ser Gly Tyr Glu Val Leu Phe Leu Thr Thr Tyr Ala Gln Ala
                195                 200                 205
Ala Asn Thr His Leu Phe Leu Leu Lys Asp Ala Gln Ile Tyr Gly Glu
                210                 215                 220
Glu Trp Gly Tyr Glu Lys Glu Asp Ile Ala Glu Phe Tyr Lys Arg Gln
225                 230                 235                 240
Leu Lys Leu Thr Gln Glu Tyr Thr Asp His Cys Val Lys Trp Tyr Asn
                245                 250                 255
Val Gly Leu Asp Lys Leu Arg Gly Ser Ser Tyr Glu Ser Trp Val Asn
                260                 265                 270
Phe Asn Arg Tyr Arg Arg Glu Met Thr Leu Thr Val Leu Asp Leu Ile
                275                 280                 285
Ala Leu Phe Pro Leu Tyr Asp Val Arg Leu Tyr Pro Lys Glu Val Lys
                290                 295                 300
Thr Glu Leu Thr Arg Asp Val Leu Thr Asp Pro Ile Val Gly Val Asn
305                 310                 315                 320
Asn Leu Arg Gly Tyr Gly Thr Thr Phe Ser Asn Ile Glu Asn Tyr Ile
                325                 330                 335
Arg Lys Pro His Leu Phe Asp Tyr Leu His Arg Ile Gln Phe His Thr
                340                 345                 350
Arg Phe Gln Pro Gly Tyr Tyr Gly Asn Asp Ser Phe Asn Tyr Trp Ser
                355                 360                 365
Gly Asn Tyr Val Ser Thr Arg Pro Ser Ile Gly Ser Asn Asp Ile Ile
                370                 375                 380
Thr Ser Pro Phe Tyr Gly Asn Lys Ser Ser Glu Pro Val Gln Asn Leu
385                 390                 395                 400
Glu Phe Asn Gly Glu Lys Val Tyr Arg Ala Val Ala Asn Thr Asn Leu
                405                 410                 415
Ala Val Trp Pro Ser Ala Val Tyr Ser Gly Val Thr Lys Val Glu Phe
                420                 425                 430
Ser Gln Tyr Asn Asp Gln Thr Asp Glu Ala Ser Thr Gln Thr Tyr Asp
                435                 440                 445
Ser Lys Arg Asn Val Gly Ala Val Ser Trp Asp Ser Ile Asp Gln Leu
                450                 455                 460
Pro Pro Glu Thr Thr Asp Glu Pro Leu Glu Lys Gly Tyr Ser His Gln
465                 470                 475                 480
Leu Asn Tyr Val Met Cys Phe Leu Met Gln Gly Ser Arg Gly Thr Ile
                485                 490                 495
Pro Val Leu Thr Trp Thr His Lys Ser Val Asp Phe Phe Asn Met Ile
                500                 505                 510
Asp Ser Lys Lys Ile Thr Gln Leu Pro Leu Val Lys Ala Tyr Lys Leu
                515                 520                 525
Gln Ser Gly Ala Ser Val Val Ala Gly Pro Arg Phe Thr Gly Gly Asp
                530                 535                 540
Ile Ile Gln Cys Thr Glu Asn Gly Ser Ala Ala Thr Ile Tyr Val Thr
545                 550                 555                 560
Pro Asp Val Ser Tyr Ser Gln Lys Tyr Arg Ala Arg Ile His Tyr Ala
                565                 570                 575
Ser Thr Ser Gln Ile Thr Phe Thr Leu Ser Leu Asp Gly Ala Pro Phe
                580                 585                 590
```

-continued

Asn Gln Tyr Tyr Phe Asp Lys Thr Ile Asn Lys Gly Asp Thr Leu Thr
            595                 600                 605

Tyr Asn Ser Phe Asn Leu Ala Ser Phe Ser Thr Pro Phe Glu Leu Ser
        610                 615                 620

Gly Asn Asn Leu Gln Ile Gly Val Thr Gly Leu Ser Ala Gly Asp Lys
625                 630                 635                 640

Val Tyr Ile Asp Lys Ile Glu Phe Ile Pro Val Asn
                645                 650

<210> SEQ ID NO 10
<211> LENGTH: 719
<212> TYPE: PRT
<213> ORGANISM: Bacillus thuringiensis

<400> SEQUENCE: 10

Met Lys Leu Lys Asn Gln Asp Lys His Gln Ser Phe Ser Ser Asn Ala
1 5 10 15

Lys Val Asp Lys Ile Ser Thr Asp Ser Leu Lys Asn Glu Thr Asp Ile
20 25 30

Glu Leu Gln Asn Ile Asn His Glu Asp Cys Leu Lys Met Ser Glu Tyr
35 40 45

Glu Asn Val Glu Pro Phe Val Ser Ala Ser Thr Ile Gln Thr Gly Ile
50 55 60

Gly Ile Ala Gly Lys Ile Leu Gly Thr Leu Gly Val Pro Phe Ala Gly
65 70 75 80

Gln Val Ala Ser Leu Tyr Ser Phe Ile Leu Gly Glu Leu Trp Pro Lys
85 90 95

Gly Lys Asn Gln Trp Glu Ile Phe Met Glu His Val Glu Glu Ile Ile
100 105 110

Asn Gln Lys Ile Ser Thr Tyr Ala Arg Asn Lys Ala Leu Thr Asp Leu
115 120 125

Lys Gly Leu Gly Asp Ala Leu Ala Val Tyr His Asp Ser Leu Glu Ser
130 135 140

Trp Val Gly Asn Arg Asn Asn Thr Arg Ala Arg Ser Val Val Lys Ser
145 150 155 160

Gln Tyr Ile Ala Leu Glu Leu Met Phe Val Gln Lys Leu Pro Ser Phe
165 170 175

Ala Val Ser Gly Glu Glu Val Pro Leu Leu Pro Ile Tyr Ala Gln Ala
180 185 190

Ala Asn Leu His Leu Leu Leu Leu Arg Asp Ala Ser Ile Phe Gly Lys
195 200 205

Glu Trp Gly Leu Ser Ser Ser Glu Ile Ser Thr Phe Tyr Asn Arg Gln
210 215 220

Val Glu Arg Ala Gly Asp Tyr Ser Asp His Cys Val Lys Trp Tyr Ser
225 230 235 240

Thr Gly Leu Asn Asn Leu Arg Gly Thr Asn Ala Glu Ser Trp Val Arg
245 250 255

Tyr Asn Gln Phe Arg Arg Asp Met Thr Leu Met Val Leu Asp Leu Val
260 265 270

Ala Leu Phe Pro Ser Tyr Asp Thr Gln Met Tyr Pro Ile Lys Thr Thr
275 280 285

Ala Gln Leu Thr Arg Glu Val Tyr Thr Asp Ala Ile Gly Thr Val His
290 295 300

Pro His Pro Ser Phe Thr Ser Thr Thr Trp Tyr Asn Asn Asn Ala Pro

```
            305                 310                 315                 320
Ser Phe Ser Ala Ile Glu Ala Val Val Arg Asn Pro His Leu Leu
                325                 330                 335

Asp Phe Leu Glu Gln Val Thr Ile Tyr Ser Leu Leu Ser Arg Trp Ser
            340                 345                 350

Asn Thr Gln Tyr Met Asn Met Trp Gly Gly His Lys Leu Glu Phe Arg
                355                 360                 365

Thr Ile Gly Gly Thr Leu Asn Ile Ser Thr Gln Gly Ser Thr Asn Thr
    370                 375                 380

Ser Ile Asn Pro Val Thr Leu Pro Phe Thr Ser Arg Asp Val Tyr Arg
385                 390                 395                 400

Thr Glu Ser Leu Ala Gly Leu Asn Leu Phe Leu Thr Gln Pro Val Asn
                405                 410                 415

Gly Val Pro Arg Val Asp Phe His Trp Lys Phe Val Thr His Pro Ile
                420                 425                 430

Ala Ser Asp Asn Phe Tyr Tyr Pro Gly Tyr Ala Gly Ile Gly Thr Gln
                435                 440                 445

Leu Gln Asp Ser Glu Asn Glu Leu Pro Pro Glu Ala Thr Gly Gln Pro
            450                 455                 460

Asn Tyr Glu Ser Tyr Ser His Arg Leu Ser His Ile Gly Leu Ile Ser
465                 470                 475                 480

Ala Ser His Val Lys Ala Leu Val Tyr Ser Trp Thr His Arg Ser Ala
                485                 490                 495

Asp Arg Thr Asn Thr Ile Glu Pro Asn Ser Ile Thr Gln Ile Pro Leu
            500                 505                 510

Val Lys Ala Phe Asn Leu Ser Ser Gly Ala Ala Val Val Arg Gly Pro
        515                 520                 525

Gly Phe Thr Gly Gly Asp Ile Leu Arg Arg Thr Asn Thr Gly Thr Phe
        530                 535                 540

Gly Asp Ile Arg Val Asn Ile Asn Pro Pro Phe Ala Gln Arg Tyr Arg
545                 550                 555                 560

Val Arg Ile Arg Tyr Ala Ser Thr Thr Asp Leu Gln Phe His Thr Ser
                565                 570                 575

Ile Asn Gly Lys Ala Ile Asn Gln Gly Asn Phe Ser Ala Thr Met Asn
            580                 585                 590

Arg Gly Glu Asp Leu Asp Tyr Lys Thr Phe Arg Thr Val Gly Phe Thr
        595                 600                 605

Thr Pro Phe Ser Phe Leu Asp Val Gln Ser Thr Phe Thr Ile Gly Ala
    610                 615                 620

Trp Asn Phe Ser Ser Gly Asn Glu Val Tyr Ile Asp Arg Ile Glu Phe
625                 630                 635                 640

Val Pro Val Glu Val Thr Tyr Glu Ala Glu Tyr Asp Phe Glu Lys Ala
                645                 650                 655

Gln Glu Lys Val Thr Ala Leu Phe Thr Ser Thr Asn Pro Arg Gly Leu
            660                 665                 670

Lys Thr Asp Val Lys Asp Tyr His Ile Asp Gln Val Ser Asn Leu Val
        675                 680                 685

Glu Ser Leu Ser Asp Glu Phe Tyr Leu Asp Glu Lys Arg Glu Leu Phe
    690                 695                 700

Glu Ile Val Lys Tyr Ala Lys Gln Leu His Ile Glu Arg Asn Met
705                 710                 715

<210> SEQ ID NO 11
```

<211> LENGTH: 1138
<212> TYPE: PRT
<213> ORGANISM: Bacillus thuringiensis

<400> SEQUENCE: 11

```
Met Asn Leu Asn Asn Leu Asp Gly Tyr Glu Asp Ser Asn Arg Thr Leu
 1               5                  10                  15
Asn Asn Ser Leu Asn Tyr Pro Thr Gln Lys Ala Leu Ser Pro Ser Leu
            20                  25                  30
Lys Asn Met Asn Tyr Gln Asp Phe Leu Ser Ile Thr Glu Arg Glu Gln
        35                  40                  45
Pro Glu Ala Leu Ala Ser Gly Asn Thr Ala Ile Asn Thr Val Val Ser
50                  55                  60
Val Thr Gly Ala Thr Leu Ser Ala Leu Gly Val Pro Gly Ala Ser Phe
65                  70                  75                  80
Ile Thr Asn Phe Tyr Leu Lys Ile Ala Gly Leu Leu Trp Pro Glu Asn
                85                  90                  95
Gly Lys Ile Trp Asp Glu Phe Met Thr Glu Val Glu Ala Leu Ile Asp
            100                 105                 110
Gln Lys Ile Glu Glu Tyr Val Arg Asn Lys Ala Ile Ala Glu Leu Asp
        115                 120                 125
Gly Leu Gly Ser Ala Leu Asp Lys Tyr Gln Lys Ala Leu Ala Asp Trp
130                 135                 140
Leu Gly Lys Gln Asp Asp Pro Glu Ala Ile Leu Ser Val Ala Thr Glu
145                 150                 155                 160
Phe Arg Ile Ile Asp Ser Leu Phe Glu Phe Ser Met Pro Ser Phe Lys
                165                 170                 175
Val Thr Gly Tyr Glu Ile Pro Leu Leu Thr Val Tyr Ala Gln Ala Ala
            180                 185                 190
Asn Leu His Leu Ala Leu Leu Arg Asp Ser Thr Leu Tyr Gly Asp Lys
        195                 200                 205
Trp Gly Phe Thr Gln Asn Asn Ile Glu Glu Asn Tyr Asn Arg Gln Lys
210                 215                 220
Lys Arg Ile Ser Glu Tyr Ser Asp His Cys Thr Lys Trp Tyr Asn Ser
225                 230                 235                 240
Gly Leu Ser Arg Leu Asn Gly Ser Thr Tyr Glu Gln Trp Ile Asn Tyr
                245                 250                 255
Asn Arg Phe Arg Arg Glu Met Ile Leu Met Ala Leu Asp Leu Val Ala
            260                 265                 270
Val Phe Pro Phe His Asp Pro Arg Arg Tyr Ser Met Glu Thr Ser Thr
        275                 280                 285
Gln Leu Thr Arg Glu Val Tyr Thr Asp Pro Val Ser Leu Ser Ile Ser
290                 295                 300
Asn Pro Asp Ile Gly Pro Ser Phe Ser Gln Met Glu Asn Thr Ala Ile
305                 310                 315                 320
Arg Thr Pro His Leu Val Asp Tyr Leu Asp Glu Leu Tyr Ile Tyr Thr
                325                 330                 335
Ser Lys Tyr Lys Ala Phe Ser His Glu Ile Gln Pro Asp Leu Phe Tyr
            340                 345                 350
Trp Ser Ala His Lys Val Ser Phe Lys Lys Ser Glu Gln Ser Asn Leu
        355                 360                 365
Tyr Thr Thr Gly Ile Tyr Gly Lys Thr Ser Gly Tyr Ile Ser Ser Gly
370                 375                 380
Ala Tyr Ser Phe His Gly Asn Asp Ile Tyr Arg Thr Leu Ala Ala Pro
```

```
            385                 390                 395                 400
Ser Val Val Tyr Pro Tyr Thr Gln Asn Tyr Gly Val Glu Gln Val
                405                 410                 415
Glu Phe Tyr Gly Val Lys Gly His Val His Tyr Arg Gly Asp Asn Lys
            420                 425                 430
Tyr Asp Leu Thr Tyr Asp Ser Ile Asp Gln Leu Pro Pro Asp Gly Glu
            435                 440                 445
Pro Ile His Glu Lys Tyr Thr His Arg Leu Cys His Ala Thr Ala Ile
            450                 455                 460
Phe Lys Ser Thr Pro Asp Tyr Asp Asn Ala Thr Ile Pro Ile Phe Ser
465                 470                 475                 480
Trp Thr His Arg Ser Ala Glu Tyr Tyr Asn Arg Ile Tyr Pro Asn Lys
                485                 490                 495
Ile Thr Lys Ile Pro Ala Val Lys Met Tyr Lys Leu Asp Asp Pro Ser
            500                 505                 510
Thr Val Val Lys Gly Pro Gly Phe Thr Gly Gly Asp Leu Val Lys Arg
            515                 520                 525
Gly Ser Thr Gly Tyr Ile Gly Asp Ile Lys Ala Thr Val Asn Ser Pro
            530                 535                 540
Leu Ser Gln Lys Tyr Arg Val Arg Val Arg Tyr Ala Thr Asn Val Ser
545                 550                 555                 560
Gly Gln Phe Asn Val Tyr Ile Asn Asp Lys Ile Thr Leu Gln Thr Lys
                565                 570                 575
Phe Gln Asn Thr Val Glu Thr Ile Gly Glu Gly Lys Asp Leu Thr Tyr
            580                 585                 590
Gly Ser Phe Gly Tyr Ile Glu Tyr Ser Thr Thr Ile Gln Phe Pro Asp
            595                 600                 605
Glu His Pro Lys Ile Thr Leu His Leu Ser Asp Leu Ser Asn Asn Ser
            610                 615                 620
Ser Phe Tyr Val Asp Ser Ile Glu Phe Ile Pro Val Asp Val Asn Tyr
625                 630                 635                 640
Ala Glu Lys Glu Lys Leu Glu Lys Ala Gln Lys Ala Val Asn Thr Leu
                645                 650                 655
Phe Thr Glu Gly Arg Asn Ala Leu Gln Lys Asp Val Thr Asp Tyr Lys
            660                 665                 670
Val Asp Gln Val Ser Ile Leu Val Asp Cys Ile Ser Gly Asp Leu Tyr
            675                 680                 685
Pro Asn Glu Lys Arg Glu Leu Gln Asn Leu Val Lys Tyr Ala Lys Arg
            690                 695                 700
Leu Ser Tyr Ser Arg Asn Leu Leu Leu Asp Pro Thr Phe Asp Ser Ile
705                 710                 715                 720
Asn Ser Ser Glu Glu Asn Gly Trp Tyr Gly Ser Asn Gly Ile Val Ile
                725                 730                 735
Gly Asn Gly Asp Phe Val Phe Lys Gly Asn Tyr Leu Ile Phe Ser Gly
            740                 745                 750
Thr Asn Asp Thr Gln Tyr Pro Thr Tyr Leu Tyr Gln Lys Ile Asp Glu
            755                 760                 765
Ser Lys Leu Lys Glu Tyr Thr Arg Tyr Lys Leu Lys Gly Phe Ile Glu
            770                 775                 780
Ser Ser Gln Asp Leu Glu Ala Tyr Val Ile Arg Tyr Asp Ala Lys His
785                 790                 795                 800
Arg Thr Leu Asp Val Ser Asp Asn Leu Leu Pro Asp Ile Leu Pro Glu
                805                 810                 815
```

```
Asn Thr Cys Gly Glu Pro Asn Arg Cys Ala Ala Gln Gln Tyr Leu Asp
            820                 825                 830
Glu Asn Pro Ser Pro Glu Cys Ser Ser Met Gln Asp Gly Ile Leu Ser
            835                 840                 845
Asp Ser His Ser Phe Ser Leu Asn Ile Asp Thr Gly Ser Ile Asn His
            850                 855                 860
Asn Glu Asn Leu Gly Ile Trp Val Leu Phe Lys Ile Ser Thr Leu Glu
865                 870                 875                 880
Gly Tyr Ala Lys Phe Gly Asn Leu Glu Val Ile Glu Asp Gly Pro Val
                885                 890                 895
Ile Gly Glu Ala Leu Ala Arg Val Lys Arg Gln Glu Thr Lys Trp Arg
                900                 905                 910
Asn Lys Leu Ala Gln Leu Thr Thr Glu Thr Gln Ala Ile Tyr Thr Arg
            915                 920                 925
Ala Lys Gln Ala Leu Asp Asn Leu Phe Ala Asn Ala Gln Asp Ser His
            930                 935                 940
Leu Lys Arg Asp Val Thr Phe Ala Glu Ile Ala Ala Ala Arg Lys Ile
945                 950                 955                 960
Val Gln Ser Ile Arg Glu Ala Tyr Met Ser Trp Leu Ser Val Val Pro
                965                 970                 975
Gly Val Asn His Pro Ile Phe Thr Glu Leu Ser Gly Arg Val Gln Arg
            980                 985                 990
Ala Phe Gln Leu Tyr Asp Val Arg Asn Val Val Arg Asn Gly Arg Phe
            995                 1000                1005
Leu Asn Gly Leu Ser Asp Trp Ile Val Thr Ser Asp Val Lys Val Gln
        1010                1015                1020
Glu Glu Asn Gly Asn Asn Val Leu Val Leu Asn Asn Trp Asp Ala Gln
1025                1030                1035                1040
Val Leu Gln Asn Val Lys Leu Tyr Gln Asp Arg Gly Tyr Ile Leu His
                1045                1050                1055
Val Thr Ala Arg Lys Ile Gly Ile Gly Glu Gly Tyr Ile Thr Ile Thr
                1060                1065                1070
Asp Glu Glu Gly His Thr Asp Gln Leu Arg Phe Thr Ala Cys Glu Glu
            1075                1080                1085
Ile Asp Ala Ser Asn Ala Phe Ile Ser Gly Tyr Ile Thr Lys Glu Leu
            1090                1095                1100
Glu Phe Phe Pro Asp Thr Glu Lys Val His Ile Glu Ile Gly Glu Thr
1105                1110                1115                1120
Glu Gly Ile Phe Leu Val Glu Ser Ile Glu Leu Phe Leu Met Glu Glu
                1125                1130                1135
Leu Cys
```

AXMI-004, A DELTA-ENDOTOXIN GENE AND METHODS FOR ITS USE

CROSS REFERENCE TO RELATED APPLICATION

This application claims the benefit of U.S. Provisional Application Ser. No. 60/448,810, filed Feb. 20, 2003, the contents of which are herein incorporated by reference in their entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiesis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiesis* strains or their insecticidal proteins can be used as environmentally acceptable insecticides to control agricultural insect pests or insect vectors for a variety of human or animal diseases.

Crystal (Cry) proteins (delta-endotoxins) from *Bacillus thuringiesis* have potent insecticidal activity against predominantly Lepidopteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus Thuringiensis* family tree. In Advanced Engineered Pesticides. Marcel Dekker, Inc., New York, N.Y.) These proteins were originally classified as CryI to CryV based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as Cry1A, Cry1B, Cry1C, etc. Even more closely related proteins within each division were given names such as Cry1C1, Cry1C2, etc.

A new nomenclature was recently described for the Cry genes based upon amino acid sequence homology rather than insect target specificity (Crickmore et al. (1998) *Microbiol. Mol. Biol. Rev.* 62:807-813). In the new classification, each toxin is assigned a unique name incorporating a primary rank (an Arabic number), a secondary rank (an uppercase letter), a tertiary rank (a lowercase letter), and a quaternary rank (another Arabic number). In the new classification, Roman numerals have been exchanged for Arabic numerals in the primary rank. Proteins with less than 45% sequence identity have different primary ranks, and the criteria for secondary and tertiary ranks are 78% and 95%, respectively.

The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol Rev.* 53:242-255). This toxin binds to apical brush border receptors in the midgut of the target larvae and inserts into the apical membrane creating ion channels or pores, resulting in larval death.

Delta-endotoxins generally have five conserved sequence domains, and three conserved structural domains (see, for example, de Maagd et al. (2001) *Trends Genetics* 17:193-199). The first conserved structural domain consists of seven alpha helices and is involved in membrane insertion and pore formation. Domain II consists of three beta-sheets arranged in a Greek key configuration, and domain III consists of two antiparallel beta-sheets in 'jelly-roll' formation (de Maagd et al. (2001) supra). Domains II and III are involved in receptor recognition and binding, and are therefore considered determinants of toxin specificity.

Because of the devastation that insects can confer, there is a continual need to discover new forms of *Bacillus thuringiesis* delta-endotoxins.

SUMMARY OF INVENTION

Compositions and methods for conferring pesticide resistance to bacteria, plants, plant cells, tissues, and seeds are provided. Compositions include isolated nucleic acid molecules encoding sequences for delta-endotoxin polypeptides, vectors comprising those nucleic acid molecules, and host cells comprising the vectors. Compositions also include isolated or recombinant polypeptide sequences of the endotoxin, compositions comprising these polypeptides, and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for optimum expression. Compositions also comprise transformed bacteria, plants, plant cells, tissues, and seeds.

In particular, the present invention provides for isolated nucleic acid molecules comprising the nucleotide sequences encoding the amino acid sequences shown in SEQ ID NOS:3 and 5 and the nucleotide sequences set forth in SEQ ID NOS:1, 2, and 4, as well as variants and fragments thereof. Nucleotide sequences that are complementary to a nucleotide sequence of the invention, or that hybridize to a sequence of the invention are also encompassed.

Methods are provided for producing the polypeptides of the invention, and for using those polypeptides for controlling or killing a lepidopteran or coleopteran pest.

The compositions and methods of the invention are useful for the production of organisms with pesticide resistance, specifically bacteria and plants. These organisms and compositions derived from them are desirable for agricultural purposes. The compositions of the invention are also useful for generating altered or improved delta-endotoxin proteins that have pesticidal activity, or for detecting the presence of delta-endotoxin proteins or nucleic acids in products or organisms.

DESCRIPTION OF FIGURES

FIGS. 1A and B shows an alignment of AXMI-004 (SEQ ID NO:3) with cry1Ac (SEQ ID NO:6), cry1Ca (SEQ ID NO:7), cry2Aa (SEQ ID NO:8), cry3Aa1 (SEQ ID NO:9), cry1Ia (SEQ ID NO: 10), and cry7Aa (SEQ ID NO: 11). Toxins having C-terminal non-toxic domains were artificially truncated as shown. Conserved group 1 is found from about amino acid residue 174 to about 196 of SEQ ID NO:3. Conserved group 2 is found from about amino acid residue 250 to about 292 of SEQ ID NO:3. Conserved group 3 is found from about amino acid residue 476 to about 521 of SEQ ID NO:3. Conserved group 4 is found from about amino acid residue 542 to about 552 of SEQ ID NO:3. Conserved group 5 is found from about amino acid residue 618 to about 628 of SEQ ID NO:3

DETAILED DESCRIPTION

Figure 2:
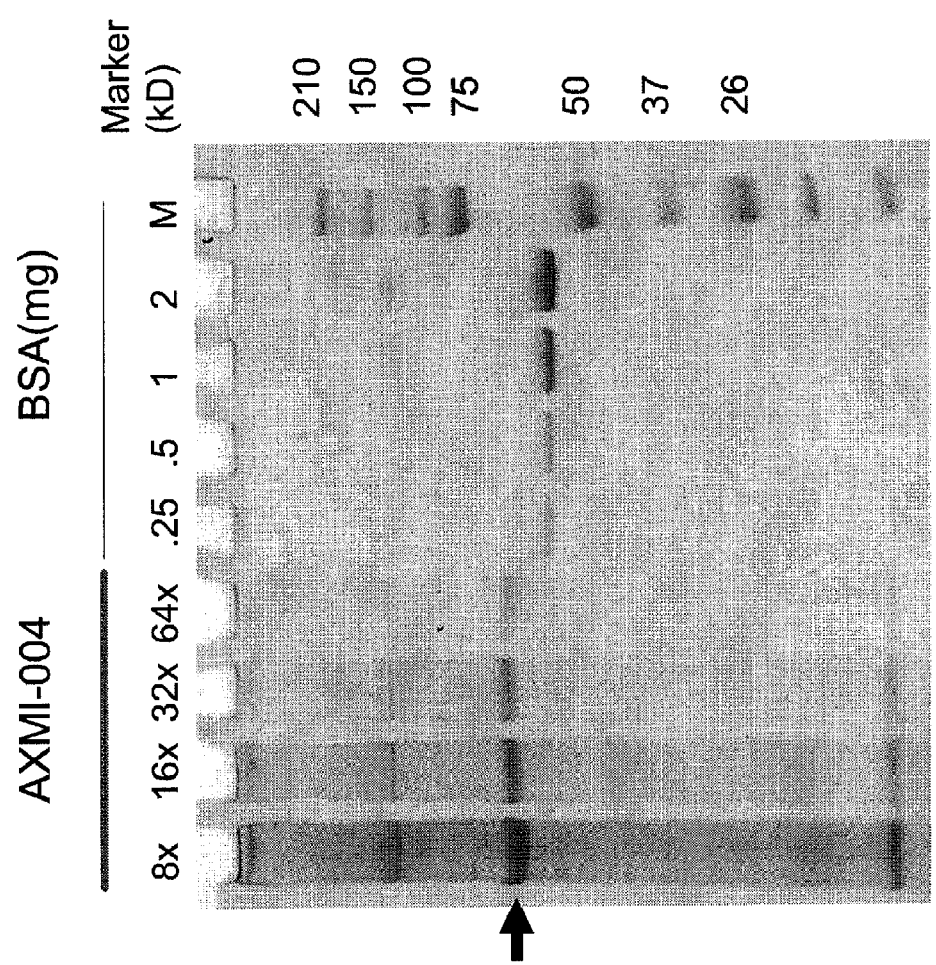
FIG. 2 shows a photograph of a 4-20% gradient SDS acrylamide gel. Lanes 1-4 contain various concentrations of sporulated Bacillus cell culture expressing 69 kD AXMI-004 protein. Lanes 5-8 contain various concentrations of BSA. Lane 9 contains a size marker. An arrow indicates the 69 kD band.

The present invention is drawn to compositions and methods for regulating pest resistance in organisms, particularly plants or plant cells. The methods involve transforming organisms with a nucleotide sequence encoding a delta-endotoxin protein of the invention. In particular, the nucleotide sequences of the invention are useful for preparing plants and microorganisms that possess pesticidal activity. Thus, transformed bacteria, plants, plant cells, plant tissues and seeds are provided. Compositions are delta-endotoxin nucleic acids and proteins of *Bacillus thuringiensis*. The sequences find use in the construction of expression vectors for subsequent transformation into organisms of interest, as probes for the isolation of other delta-endotoxin genes, and for the generation of altered pesticidal proteins by methods known in the art, such as domain swapping or DNA shuffling. The proteins find use in controlling or killing lepidopteran or coleopteran pest populations and for producing compositions with pesticidal activity.

Definitions

By "delta-endotoxin" is intended a toxin from *Bacillus thuringiesis* that has toxic activity against one or more pests, including, but not limited to, members of the Lepidoptera, Diptera, and Coleoptera orders. In some cases, delta-endotoxin proteins have been isolated from other organisms, including *Clostridium bifermentans* and *Paenibacillus popilliae*. Delta-endotoxin proteins include amino acid sequences deduced from the fill-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein. Delta-endotoxins include proteins identified as cry1 through cry43, cyt1 and cyt2, and Cyt-like toxin. There are currently over 250 known species of delta-endotoxins with a wide range of specificities and toxicities. For an expansive list see Crickmore et al. (1998), *Microbiol. Mol. Biol. Rev.* 62:807-813, and for regular updates see Crickmore et al. (2003) "*Bacillus thuringiesis* toxin nomenclature," at www.biols.susx.ac.uk/Home/Neil_Crickmore/Bt/index.

Bacterial genes, such as the AXMI-004 gene of this invention, quite often possess multiple methionine initiation codons in proximity to the start of the open reading frame. Often, translation initiation at one or more of these start codons will lead to generation of a functional protein. These start codons can include ATG codons. However, bacteria such as Bacillus sp. also recognize the codon GTG as a start codon, and proteins that initiate translation at GTG codons contain a methionine at the first amino acid. Furthermore, it is not often determined a priori which of these codons are used naturally in the bacterium. Thus, it is understood that use of one of the alternate methionine codons may also lead to generation of delta-endotoxin proteins that encode pesticidal activity. For example, an alternate start site for a delta-endotoxin protein of the invention is at base pair 385 of SEQ ID NO:1. Translation from this alternate start site results in the amino acid sequence found in SEQ ID NO:5. These delta-endotoxin proteins are encompassed in the present invention and may be used in the methods of the present invention.

By "plant cell" is intended all known forms of plant, including undifferentiated tissue (e.g. callus), suspension culture cells, protoplasts, leaf cells, root cells, phloem cells, plant seeds, pollen, propagules, embryos and the like. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a 'signal sequence' or 'leader sequence' to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. By "leader sequence" is intended any sequence that when translated, results in an amino acid sequence sufficient to trigger co-translational transport of the peptide chain to a sub-cellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one 'vector' DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has ability to incorporate, integrate and express heterologous DNA sequences or fragments in a foreign cell.

"Transgenic plants" or "transformed plants" or "stably transformed plants or cells or tissues" refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

"Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Provided herein are novel isolated nucleotide sequences that confer pesticidal activity. Also provided are the amino acid sequences for the delta-endotoxin proteins. The protein resulting from translation of this gene allows cells to control or kill pests that ingest it.

An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin-encoding nucleic acid molecule can contain less than about 5 kb, 4 kb, 3 kb, 2 kb, 1 kb, 0.5 kb, or 0.1 kb of nucleotide sequence that naturally flanks the nucleic acid molecule in genomic DNA of the cell from which the nucleic acid is derived. A delta-endotoxin protein that is substantially free of cellular material includes preparations of protein having less than about 30%, 20%, 10%, or 5% (by dry weight) of non-delta-endotoxin protein (also referred to herein as a "contaminating protein"). Various aspects of the invention are described in further detail in the following subsections.

Isolated Nucleic Acid Molecules, and Variants and Fragments Thereof

One aspect of the invention pertains to isolated nucleic acid molecules comprising nucleotide sequences encoding delta-endotoxin proteins and polypeptides or biologically active portions thereof, as well as nucleic acid molecules sufficient for use as hybridization probes to identify delta-endotoxin encoding nucleic acids. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

Nucleotide sequences encoding the proteins of the present invention include the sequences set forth in SEQ ID NOS:1, 2, and 4, and complements thereof. By "complement" is intended a nucleotide sequence that is sufficiently complementary to a given nucleotide sequence such that it can hybridize to the given nucleotide sequence to thereby form a stable duplex. The corresponding amino acid sequences for the delta-endotoxin proteins encoded by these nucleotide sequences are set forth in SEQ ID NOS:3 and 5.

Nucleic acid molecules that are fragments of these delta-endotoxin-encoding nucleotide sequences are also encompassed by the present invention. By "fragment" is intended a portion of the nucleotide sequence encoding a delta-endotoxin protein. A fragment of a nucleotide sequence may encode a biologically active portion of a delta-endotoxin protein, or it may be a fragment that can be used as a hybridization probe or PCR primer using methods disclosed below. Nucleic acid molecules that are fragments of a delta-endotoxin nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850 nucleotides, or up to the number of nucleotides present in a full-length delta-endotoxin-encoding nucleotide sequence disclosed herein (for example, 2190 nucleotides for SEQ ID NO:1, 1890 nucleotides for SEQ ID NO:2, and 1806 nucleotides for SEQ ID NO:4) depending upon the intended use. Fragments of the nucleotide sequences of the present invention will encode protein fragments that retain the biological activity of the delta-endotoxin protein and, hence, retain pesticidal activity. By "retains activity" is intended that the fragment will have at least about 30%, preferably at least about 50%, more preferably at least about 70%, even more preferably at least about 80% of the pesticidal activity of the delta-endotoxin protein. Methods for measuring pesticidal activity are well known in the art. See, for example, Czapla and Lang (1990) *J. Econ. Entomol.* 83(6): 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a delta-endotoxin encoding nucleotide sequence that encodes a biologically active portion of a protein of the invention will encode at least about 15, 25, 30, 50, 75, 100, 125, 150, 175, 200, 250, 300, 350, 400, 450, 500, 550, or 600 contiguous amino acids, or up to the total number of amino acids present in a full-length delta-endotoxin protein of the invention (for example, 629 amino acids for SEQ ID NO:3 and 601 for SEQ ID NO:5).

Preferred delta-endotoxin proteins of the present invention are encoded by a nucleotide sequence sufficiently identical to a nucleotide sequence of SEQ ID NO:1, 2, or 4. By "sufficiently identical" is intended an amino acid or nucleotide sequence that has at least about 60% or 65% sequence identity, preferably about 70% or 75% sequence identity, more preferably about 80% or 85% sequence identity, most preferably about 90%, 91%, 92%, 93%, 94%, 95%, 96%, 97%, 98% or 99% sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J Mol. Biol.* 215:403. BLAST nucleotide searches can be performed with the BLASTN program, score=100, wordlength=12, to obtain nucleotide sequences homologous to delta-endotoxin nucleic acid molecules of the invention. BLAST protein searches can be performed with the BLASTX program, score=50, wordlength=3, to obtain amino acid sequences homologous to delta-endotoxin protein molecules of the invention. To obtain gapped alignments for comparison purposes, Gapped BLAST can be utilized as described in Altschul et al. (1997) *Nucleic Acids Res*. 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. See, www.ncbi.nlm.nih.gov. Another non-limiting example of a mathematical algorithm utilized for the comparison of sequences is the ClustalW algorithm (Higgins et al. (1994) *Nucleic Acids Res*. 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the vector NTi Program Suite (Informax, Inc). After alignment of amino acid sequences with ClustalW, the percent amino acid identity can be assessed. A non-limiting example of a software program useful for analysis of ClustalW alignments is GeneDoc™. Genedoc™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG sequence alignment software package (available from Accelrys, Inc., 9865 Scranton Rd., San Diego, Calif. USA). When utilizing the ALIGN program for comparing amino acid sequences, a PAM120 weight residue table, a gap length penalty of 12, and a gap penalty of 4 can be used.

A preferred program is GAP version 10, which used the algorithm of Needleman and Wunsch (1970) supra. GAP Version 10 may be used with the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 Scoring Matrix. Equivalent programs may also be used. By "equivalent program" is intended any sequence comparison program that, for any two sequences in question, generates an alignment having identical nucleotide or amino acid residue matches and an identical percent sequence identity when compared to the corresponding alignment generated by GAP Version 10.

The invention also encompasses variant nucleic acid molecules. "Variants" of the delta-endotoxin-encoding nucleotide sequences include those sequences that encode the delta-endotoxin proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the delta-endotoxin proteins disclosed in the present invention as discussed below. Variant proteins encompassed by the present invention are biologically active, that is they continue to possess the desired biological activity of the native protein, that is, retaining pesticidal activity. By "retains activity" is intended that the variant will have at least about 30%, preferably at least about 50%, more preferably at least about 70%, even more preferably at least about 80% of the pesticidal activity of the native protein. Methods for measuring pesticidal activity are well known in the art. See, for example, Czapla and Lang (1990) *J. Econ. Entomol*. 83(6): 2480-2485; Andrews et al. (1988) *Biochem. J*. 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation into the nucleotide sequences of the invention thereby leading to changes in the amino acid sequence of the encoded delta-endotoxin proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, preferably conservative amino acid substitutions may be made at one or more predicted, preferably nonessential amino acid residues. A "nonessential" amino acid residue is a residue that can be altered from the wild-type sequence of a delta-endotoxin protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

There are generally five highly conserved regions among the delta-endotoxin proteins, concentrated largely in the center of the domain or at the junction between domains (Rajamohan et al. (1998) *Prog. Nucleic Acid Res. Mol. Biol*. 60:1-23). The blocks of conserved amino acids for various delta-endotoxins as well as consensus sequences may be found in Schnepf et al. (1998) *Microbio. Mol. Biol. Rev*. 62:775-806 and Lereclus et al. (1989) Role, Structure, and Molecular Organization of the Genes Coding for the Parasporal d-endotoxins of *Bacillus thuringiensis*. In Regulation of Procaryotic Development. Issar Smit, Slepecky, R. A., Setlow, P. American Society for Microbiology, Washington, D.C. 20006. It has been proposed that delta-endotoxins having these conserved regions may share a similar structure, consisting of three domains (Li et al. (1991) *Nature* 353: 815-821). Domain I has the highest similarity between delta-endotoxins (Bravo (1997) *J. Bacteriol*. 179: 2793-2801).

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues 103, 122, 124, 168, 170, 180, 185-188, 190, 191, 196, 204, 205, 225, 257, 262, 287, 321, 496, 518, 519, and 575 of SEQ ID NO:3. Examples of residues that are conserved but that may allow conservative amino acid substitutions and still retain activity include, for example, residues 106, 109, 110, 125, 132, 139, 152, 167, 172, 183, 194, 195, 199, 211, 233, 240, 260, 271, 329, 332, 336, 480, 521, 587, 620, and 626 of SEQ ID NO:3. However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding delta-endotoxin sequences can be identified, such sequences having substantial identity to the sequences of the invention. See, for example, Sambrook J., and Russell, D. W. (2001) *Molecular Cloning: A Laboratory Manual*. (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of a delta-endotoxin nucleotide sequence can be used to screen cDNA or genomic libraries. Methods for construction of such cDNA and genomic libraries are generally known in the art and are disclosed in Sambrook and Russell, 2001. The so-called hybridization probes may be genomic DNA fragments, cDNA fragments, RNA fragments, or other oligonucleotides, and may be labeled with a detectable group such as $^{32}P$, or any other detectable marker, such as other radioisotopes, a fluorescent compound, an enzyme, or an enzyme co-factor. Probes for hybridization can be made by labeling synthetic oligonucleotides based on the known delta-endotoxin encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, preferably about 25, more preferably at least about 50, 75, 100, 125, 150, 175, 200, 250, 300, 350, or 400 consecutive nucleotides of a delta-endotoxin-encoding nucleotide sequence of the invention or a fragment or variant thereof. Preparation of probes for hybridization is generally known in the art and is disclosed in Sambrook and Russell, 2001, herein incorporated by reference.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the delta-endotoxin sequence of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire delta-endotoxin sequence disclosed herein, or one or more portions thereof, may be used as a probe capable of specifically hybridizing to corresponding delta-endotoxin-like sequences and messenger RNAs. To achieve specific hybridization under a variety of conditions, such probes include sequences that are unique and are preferably at least about 10 nucleotides in length, and most preferably at least about 20 nucleotides in length. Such probes may be used to amplify corresponding delta-endotoxin sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem*. 138:267-284: $T_m$=81.5° C.+16.6 (log M)+0.41 (% GC)−0.61 (% form)−

500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$)for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Isolated Proteins and Variants and Fragments Thereof

Delta-endotoxin proteins are also encompassed within the present invention. By "delta-endotoxin protein" is intended a protein having the amino acid sequence set forth in SEQ ID NO:3 or 5. Fragments, biologically active portions, and variants thereof are also provided, and may be used to practice the methods of the present invention.

"Fragments" or "biologically active portions" include polypeptide fragments comprising a portion of an amino acid sequence encoding a delta-endotoxin protein as set forth in SEQ ID NO:3 or 5 and that retains pesticidal activity. A biologically active portion of a delta-endotoxin protein can be a polypeptide that is, for example, 10, 25, 50, 100 or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83(6): 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:3 or 5. The invention encompasses other fragments, however, such as any fragment in the protein greater than about 10, 20, 30, 50, 100, 150, 200, 250, 300, 350, 400, 450, 500, 550, and 600 amino acids.

By "variants" is intended proteins or polypeptides having an amino acid sequence that is at least about 60%, 65%, preferably about 70%, 75%, more preferably about 80%, 85%, most preferably about 90%, 91%, 92%, 93%, 94%, 95%, 96%, 97%, 98% or 99% identical to the amino acid sequence of SEQ ID NO:3 or 5. Variants also include polypeptides encoded by a nucleic acid molecule that hybridizes to the nucleic acid molecule of SEQ ID NO:1, 2, or 4, or a complement thereof, under stringent conditions. Such variants generally retain pesticidal activity. Variants include polypeptides that differ in amino acid sequence due to mutagenesis. Variant proteins encompassed by the present invention are biologically active, that is they continue to possess the desired biological activity of the native protein, that is, retaining pesticidal activity. Methods for measuring pesticidal activity are well known in the art. See, for example, Czapla and Lang (1990) *J. Econ. Entomol.* 83(6): 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Altered or Improved Variants

It is recognized that DNA sequences of a delta-endotoxin may be altered by various methods, and that these alterations may result in DNA sequences encoding proteins with amino acid sequences different than that encoded by the delta-endotoxin of the present invention. This protein may be altered in various ways including amino acid substitutions, deletions, truncations, and insertions. Methods for such manipulations are generally known in the art. For example, amino acid sequence variants of the delta-endotoxin protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of delta-endotoxin to confer pesticidal activity may be improved by the use of such techniques upon the compositions of this invention. For example, one may express delta-endotoxin in host cells that exhibit high rates of base misincorporation during DNA replication, such as XL-1 Red (Stratagene). After propagation in such strains, one can isolate the delta-endotoxin DNA (for example by preparing plasmid DNA, or by amplifying by PCR and cloning the resulting PCR fragment into a vector), culture the delta-endotoxin mutations in a non-mutagenic strain, and identify mutated delta-endotoxin genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different delta-endotoxin protein coding regions can be used to create a new delta-endotoxin protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the delta-endotoxin gene of the invention and other known delta-endotoxin genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech*. 15:436-438; Moore et al. (1997) *J. Mol. Biol*. 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered delta-endotoxin proteins. Domains II and III may be swapped between delta-endotoxin proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol*. 67:5328-5330; de Maagd et al. (1996) *Appl. Environ. Microbiol*. 62: 1537-1543; Ge et al. (1991) *J. Biol. Chem*. 266:17954-17958; Schnepf et al. (1990) *J. Biol. Chem*. 265:20923-20930; Rang et al. 91999) *Appl. Environ. Micriobiol*. 65:2918-2925).

Plant Transformation

Transformation of plant cells can be accomplished by one of several techniques known in the art. First, one engineers the delta-endotoxin gene in a way that allows its expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this 'plant expression cassette' will be inserted into a 'plant transformation vector'. This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as 'binary vectors'. Binary vectors as well as vectors with helper plasmids are most often used for Agrobacterium-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a 'gene of interest' (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the gene of interest are located between the left and right borders. Often a second plasmid vector contains the trans-acting factors that mediate T-DNA transfer from Agrobacterium to plant cells. This plasmid often contains the virulence functions (Vir genes) that allow infection of plant cells by *Agrobacterium*, and transfer of DNA by cleavage at border sequences and vir-mediated DNA transfer, as in understood in the art (Hellens and Mullineaux (2000) *Trends in Plant Science*, 5:446-451). Several types of Agrobacterium strains (e.g. LBA4404, GV3101, EHA101, EHA105, etc.) can be used for plant transformation. The second plasmid vector is not necessary for transforming the plants by other methods such as microprojection, microinjection, electroporation, polyethelene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6: 271-282; Ishida et al. (1996) *Nature Biotechnology* 14: 745-750). Explants are typically transferred to a fresh supply of the same medium and cultured routinely. A general description of the techniques and methods for generating transgenic plantlets are found in Ayres and Park, 1994 (*Critical Reviews in Plant Science* 13:219-239) and Bommineni and Jauhar, 1997 (*Maydica* 42:107-120). Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Generation of transgenic plants may be performed by one of several methods, including but not limited to introduction of heterologous DNA by *Agrobacterium* into plant cells (*Agrobacterium*-mediated transformation), bombardment of plant cells with heterologous foreign DNA adhered to particles, and various other non-particle direct-mediated methods (e.g. Hiei et al. (1994) *The Plant Journal* 6:271-282; Ishida et al. (1996) *Nature Biotechnology* 14:745-750; Ayres and Park (1994) *Critical Reviews in Plant Science* 13:219-239; Bommineni and Jauhar (1997) *Maydica* 42:107-120) to transfer DNA.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320-334), electroporation (Riggs et al. (1986) *Proc. Natl. Acad. Sci. USA* 83:5602-5606, *Agrobacterium*-mediated transformation (U.S. Pat. No. 5,563,055; U.S. Pat. No. 5,981,840), direct gene transfer (Paszkowski et al. (1984) *EMBO J.* 3:2717-2722), and ballistic particle acceleration (see, for example, U.S. Pat. No. 4,945,050; U.S. Pat. No. 5,879,918; U.S. Pat. No. 5,886,244; U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Biotechnology* 6:923-926); aerosol beam transformation (U.S. Published Application No. 20010026941; U.S. Pat. No. 4,945,050; International Publication No. WO 91/00915; U.S. Published Application No. 2002015066); and Lec1 transformation (WO 00/28058). Also see, Weissinger et al. (1988) *Ann. Rev. Genet.* 22:421-477; Sanford et al. (1987) *Particulate Science and Technology* 5:27-37; Christou et al. (1988) *Plant Physiol.* 87:671-674; McCabe et al. (1988) *Bio/Technology* 6:923-926; Finer and McMullen (1991) *In Vitro Cell Dev. Biol.* 27P:175-182; Singh et al. (1998) *Theor. Appl. Genet.* 96:319-324; Datta et al. (1990) *Biotechnology* 8:736-740; Klein et al. (1988) *Proc. Natl. Acad. Sci. USA* 85:4305-4309; U.S. Pat. No. 5,240,855; U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin); Klein et al. (1988) *Plant Physiol.* 91:440-444; Hooykaas-Van Slogteren et al. (1984) *Nature* (London) 311:763-764; U.S. Pat. No. 5,736,369; Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209; Kaeppler et al. (1990) *Plant Cell Reports* 9:415-418 and Kaeppler et al. (1992) *Theor. Appl. Genet.* 84:560-566; D'Halluin et al. (1992) *Plant Cell* 4:1495-1505; Li et al. (1993) *Plant Cell Reports* 12:250-255 and Christou and Ford (1995) *Annals of Botany* 75:407-413 (rice); Osjoda et al. (1996) *Nature Biotechnology* 14:745-750; all of which are herein incorporated by reference.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Then molecular and biochemical methods will be used for confirming the presence of the integrated heterologous gene of interest in the genome of transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

The delta-endotoxin sequences of the invention may be provided in expression cassettes for expression in the plant of interest. The cassette will include 5' and 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

Such an expression cassette is provided with a plurality of restriction sites for insertion of the delta-endotoxin sequence to be under the transcriptional regulation of the regulatory regions.

The expression cassette will include in the 5'-3' direction of transcription, a transcriptional and translational initiation region (i.e., a promoter), a DNA sequence of the invention, and a transcriptional and translational termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably-linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are known in the art for synthesizing host-preferred genes. See, for example, U.S. Pat. Nos. 6,320,100, 6,075,185; 5,380,831; and 5,436,391, U.S. Published Application Nos. 20040005600 and 20010003849, and Murray et al. (1989) *Nucleic Acids Res.* 17:477-498, herein incorporated by reference.

In one embodiment, the nucleic acids of interest are targeted to the chloroplast for expression. In this manner, where the nucleic acid of interest is not directly inserted into the chloroplast, the expression cassette will additionally contain a nucleic acid encoding a transit peptide to direct the gene product of interest to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR Analysis: PCR analysis is a rapid method to screen transformed cells, tissue or shoots for the presence of incorporated gene at the earlier stage before transplanting into the soil (Sambrook and Russell, 2001) PCR is carried out using oligonucleotide primers specific to the gene of interest or Agrobacterium vector background, etc.

Southern Analysis: Plant transformation is confirmed by Southern blot analysis of genomic DNA (Sambrook and Russell, 2001). In general, total DNA is extracted from the transformant, digested with appropriate restriction enzymes, fractionated in an agarose gel and transferred to a nitrocellulose or nylon membrane. The membrane or "blot" then is probed with, for example, radiolabeled $^{32}P$ target DNA fragment to confirm the integration of introduced gene in the plant genome according to standard techniques (Sambrook and Russell, 2001. *Molecular Cloning: A Laboratory Manual*. Cold Spring Harbor Laboratory Press, Cold Spring Harbor, N.Y.).

Northern Analysis: RNA is isolated from specific tissues of transformant, fractionated in a formaldehyde agarose gel, blotted onto a nylon filter according to standard procedures that are routinely used in the art (Sambrook, J., and Russell, D. W. 2001. *Molecular Cloning: A Laboratory Manual*, Cold Spring Harbor Laboratory Press, Cold Spring Harbor, N.Y.). Expression of RNA encoded by the delta-endotoxin is then tested by hybridizing the filter to a radioactive probe derived from a delta-endotoxin, by methods known in the art (Sambrook and Russell, 2001)

Western blot and Biochemical assays: Western blot and biochemical assays and the like may be carried out on the transgenic plants to confirm the determine the presence of protein encoded by the delta-endotoxin gene by standard procedures (Sambrook, J., and Russell, D. W. 2001. *Molecular Cloning: A Laboratory Manual*, Cold Spring Harbor Laboratory Press, Cold Spring Harbor, N.Y.) using antibodies that bind to one or more epitopes present on the delta-endotoxin protein.

Pesticidal Activity in Plants

In another aspect of the invention, one may generate transgenic plants expressing delta-endotoxin that have pesticidal activity. Methods described above by way of example may be utilized to generate transgenic plants, but the manner in which the transgenic plant cells are generated is not critical to this invention. Methods known or described in the art such as *Agrobacterium*-mediated transformation, aerosol beam, biolistic transformation, and non-particle-mediated methods may be used at the discretion of the experimenter. Plants expressing delta-endotoxin may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene).

Fertile plants expressing delta-endotoxin may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

Use in Pesticidal Control

General methods for employing the strains of the invention in pesticide control or in engineering other organisms as pesticidal agents are known in the art. See, for example U.S. Pat. No. 5,039,523 and EP 0480762A2.

The *Bacillus* strains of the invention or the microorganisms that have been genetically altered to contain the pesticidal gene and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a heterologous gene into a cellular host. Expression of the heterologous gene results, directly or indirectly, in the intracellular production and maintenance of the pesticide. In one aspect of this invention, these cells are then treated under conditions that prolong the activity of the toxin produced in the cell when the cell is applied to the environment of target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing the genes of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, mollusocides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible “baits” or fashioned into pest “traps” to permit feeding or ingestion by a target pest of the pesticidal formulation.

Preferred methods of applying an active ingredient of the present invention or an agrochemical composition of the present invention which contains at least one of the pesticidal proteins produced by the bacterial strains of the present invention are leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be preparable by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By “pesticidally-effective amount” is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term “agriculturally-acceptable carrier” covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

“Pest” includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

Insect pests include insects selected from the orders Coleoptera, Diptera, Hymenoptera, Lepidoptera, Mallophaga, Homoptera, Hemiptera, Orthoptera, Thysanoptera, Dermaptera, Isoptera, Anoplura, Siphonaptera, Trichoptera, etc., particularly Coleoptera and Lepidoptera. Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafininer; *Anaphothrips*

*obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; Eleodes, Conoderus, and Aeolus spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, armyworm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

The following examples are offered by way of illustration and not by way of limitation.

EXPERIMENTAL

EXAMPLE 1

Extraction of Plasmid DNA

A pure culture of strain ATX13002 was grown in large quantities of rich media. The culture was spun to harvest the cell pellet. The cell pellet was then prepared by treatment with SDS allowing breakage of the cell wall and release of DNA. Proteins and large genomic DNA was then precipitated by a high salt concentration. The plasmid DNA was then taken and precipitated by standard ethanol precipitation. The plasmid DNA was separated from any remaining chromosomal DNA by high-speed centrifugation through a cesium chloride gradient. The DNA was visualized in the gradient by UV light and the lower plasmid band was extracted using a syringe. This band contained the plasmid DNA from strain ATX13002. Quality of the DNA was checked by visualization on an agarose gel.

EXAMPLE 2

Cloning of Genes

The purified plasmid DNA was sheared into 5-10 kb sized fragments and the 5' and 3' single stranded overhangs repaired using T4 DNA polymerase and Klenow fragment in the presence of all four dNTPs, as known in the art. Phosphates were then attached to the 5' ends by treatment with T4 polynucleotide kinase, as known in the art. The repaired DNA fragments were then ligated overnight into a standard high copy vector (i.e. pBluescript SK+), suitably prepared to accept the inserts as known in the art (for example by digestion with a restriction enzyme producing blunt ends).

The quality of the library was analyzed by digesting a subset of clones with a restriction enzyme known to have a cleavage site flanking the cloning site. A high percentage of clones were determined to contain inserts, with an average insert size of 5-6 kb.

EXAMPLE 3

High Throughput Sequencing of Library Plates

Once the shotgun library quality was checked and confirmed, colonies were grown in a rich broth in 2 ml 96-well blocks overnight at 37° C. at a shaking speed of 350 rpm.

The blocks were spun to harvest the cells to the bottom of the block. The blocks were then prepared by standard alkaline lysis prep in a high throughput format.

The end sequences of clones from this library were then determined for a large number of clones from each block in the following way: The DNA sequence of each clone chosen for analysis was determined using the fluorescent dye terminator sequencing technique (Applied Biosystems) and standard primers flanking each side of the cloning site. Once the reactions had been carried out in the thermocycler, the DNA was precipitated using standard ethanol precipitation. The DNA was resuspended in water and loaded onto a capillary sequencing machine. Each library plate of DNA was sequenced from either end of the cloning site, yielding two reads per plate over each insert.

EXAMPLE 4

Assembly and Screening of Sequencing Data

DNA sequences obtained were compiled into an assembly project and aligned together to form contigs. This can be done efficiently using a computer program, such as Vector NTi, or alternatively by using the Pred/Phrap suite of DNA alignment and analysis programs. These contigs, along with any individual read that may not have been added to a contig, were compared to a compiled database of all classes of known pesticidal genes. Contigs or individual reads identified as having identity to a known endotoxin or pesticidal gene were analyzed further. A single clone, pAX004, containing DNA showing homology to known endotoxin genes. Therefore, pAX004 was selected for further sequencing.

EXAMPLE 5

Sequencing of pAX004 and Identification of AXMI-004

Primers were designed to anneal to pAX004, in a manner such that DNA sequences generated from such primers will overlap existing DNA sequence of this clone(s). This process, known as "oligo walking", is well known in the art. This process was utilized to determine the entire DNA sequence of the region exhibiting homology to a known endotoxin gene. In the case of pAX004, this process was used to determine the DNA sequence of the entire clone, resulting in a single nucleotide sequence. The completed DNA sequence was then placed back into the original large assembly for further validation. This allowed incorporation of more DNA sequence reads into the contig, resulting in 6-7 reads of coverage over the entire region.

Analysis of the DNA sequence of pAX004 by methods known in the art identified an open reading frame with homology to known delta endotoxin genes. This open reading frame is designated as AXMI-004. The DNA sequence of AXMI-004 is provided as SEQ ID NO:1, and the amino acid sequence of the predicted AMXI-004 protein is provided as SEQ ID NO:3. An alternate start site for AXMI-004 at nucleotide 385 of SEQ ID NO:1 generates the amino acid sequence provided as SEQ ID NO:5.

EXAMPLE 6

Homology of AXMI-004 to Known Endotoxin Genes

Searches of DNA and protein databases with the DNA sequence and amino acid sequence of AXMI-004 reveal that AXMI-004 is homologous to known endotoxins. FIG. 1 shows an alignment of AXMI-004 with several endotoxins. Blast searches identify cry1Ca as having the strongest block of homology, though the overall sequence identity in the toxic domain is only 43% (see Table 1).

Alignment of AXMI-004 amino acid sequence with the highest scoring proteins identified by blast search.

TABLE 1

| | Amino Acid Identity of AXMI-004 with Exemplary Endotoxin Classes | |
|---|---|---|
| Endotoxin | Percent Amino Acid Identity to AXMI-004 | Percent Amino Acid Identity in Toxic Domains |
| cry1Ac* | 17% | 30% |
| cry1Ca* | 24% | 43% |
| cry2Aa | 12% | 12% |
| cry3Aa | 33% | 33% |
| cry1Ia | 35% | 37% |
| cry7Aa | 19% | 31% |

EXAMPLE 7

Assays for Pesticidal Activity

The ability of a pesticidal protein to act as a pesticide upon a pest is often assessed in a number of ways. One way well known in the art is to perform a feeding assay. In such a feeding assay, one exposes the pest to a sample containing either compounds to be tested, or control samples. Often this is performed by placing the material to be tested, or a suitable dilution of such material, onto a material that the pest will ingest, such as an artificial diet. The material to be tested may be composed. of a liquid, solid, or slurry. The material to be tested may be placed upon the surface and then allowed to dry. Alternatively, the material to be tested may be mixed with a molten artificial diet, then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouthparts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson, J. L. & H. K. Preisler. 1992. *Pesticide bioassays with arthropods*. CRC, Boca Raton, Fla. Alternatively, assays are commonly described in the journals "Arthropod Management Tests"

and "Journal of Economic Entomology" or by discussion with members of the Entomological Society of America (ESA).

EXAMPLE 8

Expression of AXMI-004 in *Bacillus*

The 1,890 base pair insecticidal AXMI-004 gene was amplified by PCR from pAX004, and cloned into the *Bacillus* Expression vector pAX916 by methods well known in the art. The resulting clone, pAX920, expressed AXMI-004 protein when transformed into cells of a cry(−) *Bacillus thuringiesis* strain (see FIG. 2). The *Bacillus* strain containing pAX920 and expressing the 69 kD AXMI-004 insecticidal protein may be cultured on a variety of conventional growth media. A *Bacillus* strain containing pAX920 was grown in CYS media (10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$), until sporulation was evident by microscopic examination. Samples were prepared, and AXMI-004 was tested for insecticidal activity in bioassays against important insect pests.

Methods

To prepare CYS media: 10 g/l Bacto-casitone; 3 g/l yeast extract; 6 g/l $KH_2PO_4$; 14 g/l $K_2HPO_4$; 0.5 mM $MgSO_4$; 0.05 mM $MnCl_2$; 0.05 mM $FeSO_4$. The CYS mix should be pH 7, if adjustment is necessary. NaOH or HCl are preferred. The media is then autoclaved and 100 ml of 10×filtered glucose is added after autoclaving. If the resultant solution is cloudy it can be stirred at room temperature to clear.

EXAMPLE 9

N-terminal Amino Acid Seciuence of AXMI-004 Expressed in *Bacillus*

Analysis of AXMI-004 expressed in *Bacillus* suggested that the protein product detected in these cultures may be reduced in size relative to the full-length AXMI-004 protein. Since many endotoxin proteins are cleaved at the N-terminus after expression in *Bacillus*, we determined the N-terminus of the AXMI-004 protein resulting from *Bacillus* expression. Protein samples from AXMI-004 were separated on PAGE gels, and the protein transferred to PVDF membrane by methods known in the art. The protein band corresponding to AXMI-004 was excised. The N-terminal amino acid sequence of this protein was determined by serial Edman degradation as known in the art. The sequence obtained was as follows:

ERFDKNDALE (SEQ ID NO:11)

Comparison of this amino acid sequence with the sequence of the full length AXMI-004 (SEQ ID NO:3) demonstrates that this amino sequence results from internal cleavage of the AXMI-004 after expression in Bacillus, resulting in a protein with an N-terminus corresponding to amino acid 28 of SEQ ID NO:3 (disclosed as SEQ ID NO:5).

EXAMPLE 10

Bioassay of AXMI-004 on Insects Pests

Insecticidal activity of AXMI-004 was established utilizing accepted bioassay procedures using a sporulated *Bacillus* cell culture lysate expressing AXMI-004. The *Bacillus* culture was grown in 50 ml CYS media for both standard bioassay and $LC_{50}$ bioassays. The cultures were then grown for 2 to 3 days at 30° C., 250 rpm until the cells were sporulated. Sporulation was determined by examining microscopically for the presence of spores. AXMI-004 protein samples were prepared by centrifugation of the sporulated cultures at 12,000×g for 10 min. The pellet was collected and resuspended in 4 ml 20 mM Tris-HCl, pH 8.0. The suspension was sonicated for 20 seconds (at top power using a micro probe) while placing the tube on ice. The protein concentration of the sample was determined by electrophoresis on an SDS 4-20% gradient acrylamide gel along with a known quantity of bovine serum albumin (BSA) (FIG. 2). The concentration of AXMI-004 was determined to be 0.4 μg/ul.

AXMI-004 insecticidal activity was tested using a surface treatment bioassay with artificial diet (Multiple Species diet, Southland Products, Lake Village, Ark.) prepared as known in the art. Bioassays were carried out by applying the *Bacillus* culture expressing AXMI-004 to the diet surface and allowing the surface to air-dry. Standard bioassays utilized five eggs per well and $LC_{50}$ bioassays utilized ten neonate insect larvae per well. The eggs or larvae were applied using a fine tip paintbrush. Standard surface bioassays were carried out in 24 well tissue culture plates. 40ul of each sample was applied to each well. Since each well has a surface area of 2 $cm^2$ (plate source), a 40 μl cell lysate sample contained approximately 0.4 ug/ul AXMI-004. Bioassays where the $LC_{50}$ was determined were done in 48 well tissue culture plates, each well representing a surface area of 1 $cm^2$ (source) using approximately 20ul of 0.4 μg/ul AXMI-004 per well. The final amount of AXMI-004 protein in each bioassay was approximately 8 μg/$cm^2$. Bioassay trays were sealed with Breathe Easy Sealing Tape (Diversified Biotech, Boston Mass.). Control samples included media only samples, and wells that were not treated with samples. Bioassays were then held for five days in the dark at 25° C. and 65% relative humidity and results recorded.

TABLE 2

Insecticidal Activity of AXMI-004

| Insect (Latin Name) | Common Name | Activity of AXMI-004 |
| --- | --- | --- |
| *Ostrinia nubilalis* | European Corn Borer | 100% mortality |
| *Agrotis ipsilon* | Black Cutworm | Stunted |
| *Heliothis zea* | Corn Earworm | Stunted |
| *Spodoptera frugiperda* | Fall Armyworm | Stunted |
| *Heliothis virescens* | Tobacco Budworm | 100% mortality |
| *Pectinophora gossypiella* | Pink Bollworm | 75% mortality |
| *Manduca sexta* | Tobacco Hornworm | 100% mortality |
| *Trichoplusia ni* | Cabbage Looper | 100% mortality |

AXMI-004 showed strong insecticidal activity (100% mortality) against *Ostrinia nubilalis* and *Heliothis virescens*. AXMI-004 also showed insecticidal activity of 50-75% mortality against *Pectinophora gossypiella*. A concentration of 43 μg/$cm^2$ AXMI-004 gave 70% mortality against *Pectinophora gossypiella*. AXMI-004 severely stunted the growth of *Agrotis ipsilon*, *Heliothis zea*, and *Spodoptera frugiperda*.

EXAMPLE 11

Quantitation of AXMI-004 Insecticidal Activity Against *Heliothis Virescens* and *Ostrinia Nubilalis*

The $LC_{50}$ of AXMI-004 protein on *Ostrinia nubilalis* and *Heliothis virescens* larvae were determined by testing a range of AXMI-004 protein concentrations in insect bioassays, and applying these protein samples to the surface of insect diet. Mortality was recorded at each protein concentration and analyzed using a Probit analysis program. Results were significant at the 95% confidence interval. Since assays were performed by surface contamination, $LC_{50}$s were determined assuming that the entire protein sample remained at the surface during the assay, with little diffusion below the level ingested by the insects. Thus, the values determined may somewhat underestimate the toxicity of the AXMI-004 protein on the tested insects.

TABLE 3

$LC_{50}$ of AXMI-004 on *Ostrinia nubilalis*

| AXMI-004 (μg/ml) | # dead/total | % Mortality |
|---|---|---|
| 1000 | 40/46 | 86.9 |
| 500 | 28/45 | 62.2 |
| 250 | 16/43 | 32.7 |
| 125 | 12/38 | 31.6 |

$LC_{50}$ = 297 ng/cm$^2$;
95% CI = 218-384.

TABLE 4

$LC_{50}$ of AXMI-004 on *Heliothis virescens*

| AXMI-004 (μg/ml) | # dead/total | % Mortality |
|---|---|---|
| 8000 | 35/47 | 74.5 |
| 4000 | 26/44 | 59.1 |
| 2000 | 18/42 | 42.9 |
| 1000 | 6/27 | 22.2 |
| 500 | 4/36 | 11.1 |
| 250 | 2/37 | 5.4 |

$LC_{50}$ = 2874 ng/cm$^2$;
95% CI = 2189-3933

EXAMPLE 12

Quantitation of AXMI-004 Insecticidal Activity Against *Lygus Lineolaris*

Bacterial lysates were prepared by growing the *Bacillus* in 50 ml of CYS media for 60 hours. The *Bacillus* culture was then centrifuged at 12,000 rpm for ten minutes and the supernatant discarded. The pellet was resuspended in 5 ml of 20 mM Tris HCl at pH 8.

Bioassays were performed by cutting both the tip and the cap off an Eppendorf tube to form a feeding chamber. The insecticidal protein or control was presented to the insect in a solution that was poured into the cap and covered with parafilm (Pechiney Plastic Packaging, Chicago Ill.) that the insect could pierce upon feeding. The Eppendorf tube was placed back on the cap top down and 1$^{st}$ or 2$^{nd}$ instar *Lygus* nymphs were placed into the Eppendorf chamber with a fine tip brush. The cut Eppendorf tube tip was sealed with paraflim creating an assay chamber. The resultant assay chamber was incubated at ambient temperature cap side down. Insecticidal proteins were tested in a solution of 15% glucose at a concentration of 66 ug/ml.

TABLE 5

Insecticidal Activity of AXMI-004 on *Lygus lineolaris*

| Protein | No. Dead/Total | % Mortality |
|---|---|---|
| AXMI-004 | 2/4 | 50% |
| Control | 0/9 | 0% |

EXAMPLE 13

Vectoring of AXMI-004 for Plant Expression

The AXMI-004 coding region DNA is operably connected with appropriate promoter and terminator sequences for expression in plants. Such sequences are well known in the art and may include the rice actin promoter or maize ubiquitin promoter for expression in monocots, the *Arabidopsis* UBQ3 promoter or CaMV 35S promoter for expression in dicots, and the nos or PinII terminators. Techniques for producing and confirming promoter-gene-terminator constructs also are well known in the art.

The plant expression cassettes described above are combined with an appropriate plant selectable marker to aid in the selections of transformed cells and tissues, and ligated into plant transformation vectors. These may include binary vectors from *Agrobacterium*-mediated transformation or simple plasmid vectors for aerosol or biolistic transformation.

EXAMPLE 14

Transformation of Maize Cells with AXMI-004

Maize ears are collected 8-12 days after pollination. Embryos are isolated from the ears, and those embryos 0.8-1.5 mm in size are used for transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casaminoacids; 50 g/L sucrose; 1 mL/L (of 1 mg/mL Stock) 2,4-D), and incubated overnight at 25° C. in the dark.

The resulting explants are transferred to mesh squares (30-40 per plate), transferred onto osmotic media for 30-45 minutes, then transferred to a beaming plate (see, for example, PCT Publication No. WO/0138514 and U.S. Pat. No. 5,240,842).

DNA constructs designed to express AXMI-004 in plant cells are accelerated into plant tissue using an aerosol beam accelerator, using conditions essentially as described in PCT Publication No. WO/0138514. After beaming, embryos are incubated for 30 min on osmotic media, then placed onto incubation media overnight at 25° C. in the dark. To avoid unduly damaging beamed explants, they are incubated for at least 24 hours prior to transfer to recovery media. Embryos are then spread onto recovery period media, for 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

| DN62A5S Media | | |
|---|---|---|
| Components | per liter | Source |
| Chu'S N6 Basal Salt Mixture (Prod. No. C 416) | 3.98 g/L | Phytotechnology Labs |
| Chu's N6 Vitamin Solution (Prod. No. C 149) | 1 mL/L (of 1000 × Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casaminoacids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

Adjust the pH of the solution to pH to 5.8 with 1N KOH/1N KCl, add Gelrite (Sigma) to 3g/L, and autoclave. After cooling to 50° C., add 2 ml/L of a 5 mg/ml stock solution of Silver Nitrate (Phytotechnology Labs). Recipe yields about 20 plates.

EXAMPLE 15

Transformation of AXMI-004 into Plant Cells by Agrobacterium-Mediated Transformation Ears are collected 8-12 days after pollination. Embryos are isolated from the ears, and those embryos 0.8-1.5 mm in size are used for transformation. Embryos are plated scutellum side-up on a suitable incubation media, and incubated overnight at 25° C. in the dark. However, it is not necessary per se to incubate the embryos overnight. Embryos are contacted with an Agrobacterium strain containing the appropriate vectors for Ti plasmid mediated transfer for 5-10 min, and then plated onto co-cultivation media for 3 days (25° C. in the dark). After co-cultivation, explants are transferred to recovery period media for five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art. The resulting shoots are allowed to root on rooting media, and the resulting plants are transferred to nursery pots and propagated as transgenic plants.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleic acid molecule selected from the group consisting of:
   a) a nucleic acid molecule comprising the nucleotide sequence of SEQ ID NO:1, 2, or 4; and,
   b) a nucleic acid molecule which encodes a polypeptide comprising the amino acid sequence of SEQ ID NO:3 or 5.

2. The isolated nucleic acid molecule of claim 1, wherein said nucleotide sequence is a synthetic sequence that has been designed for expression in a plant.

3. The nucleic acid molecule of claim 2, wherein said synthetic sequence has an increased GC content relative to the GC content of SEQ ID NO:1, 2, or 4.

4. A vector comprising the nucleic acid molecule of claim 1.

5. The vector of claim 4, further comprising a nucleic acid molecule encoding a heterologous polypeptide.

6. A host cell that contains the vector of claim 4.

7. The host cell of claim 6 that is a bacterial host cell.

8. The host cell of claim 6 that is a plant cell.

9. A transgenic plant comprising the host cell of claim 8.

10. The transgenic plant of claim 9, wherein said plant is selected from the group consisting of maize, sorghum, wheat, sunflower, tomato, crucifers, peppers, potato, cotton, rice, soybean, sugarbeet, sugarcane, tobacco, barley, and oilseed rape.

11. A transgenic seed comprising the nucleic acid molecule of claim 1.

12. A method for producing a polypeptide with pesticidal activity, the method comprising culturing the host cell of claim 6 under conditions in which the nucleic acid molecule encoding the polypeptide is expressed.

13. A plant having stably incorporated into its genome a DNA construct comprising a nucleotide sequence that encodes a protein having pesticidal activity, wherein said nucleotide sequence is selected from the group consisting of:
  a) the nucleotide sequence of SEQ ID NO:1, 2, or 4; and,
  b) a nucleotide sequence encoding a polypeptide comprising the amino acid sequence of SEQ ID NO:3 or 5;
wherein said nucleotide sequence is operably linked to a promoter that drives expression of a coding sequence in a plant cell.

14. A plant cell having stably incorporated into its genome a DNA construct comprising a nucleotide sequence that encodes a protein having pesticidal activity, wherein said nucleotide sequence is selected from the group consisting of:
  a) the nucleotide sequence of SEQ ID NO:1, 2, or 4; and
  b) a nucleotide sequence encoding a polypeptide comprising the amino acid sequence of SEQ ID NO:3 or 5;
wherein said nucleotide sequence is operably linked to a promoter that drives expression of a coding sequence in a plant cell.

* * * * *